US011154404B2

(12) United States Patent
Freedman et al.

(10) Patent No.: US 11,154,404 B2
(45) Date of Patent: Oct. 26, 2021

(54) SPINAL FIXATION SYSTEM

(71) Applicant: Mayo Foundation for Medical Education and Research, Rochester, MN (US)

(72) Inventors: Brett Freedman, Rochester, MN (US); April V. Krivoniak, Greensburg, PA (US); Kendall D. Dennis, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 298 days.

(21) Appl. No.: 16/331,706

(22) PCT Filed: Sep. 8, 2017

(86) PCT No.: PCT/US2017/050775
§ 371 (c)(1),
(2) Date: Mar. 8, 2019

(87) PCT Pub. No.: WO2018/049227
PCT Pub. Date: Mar. 15, 2018

(65) Prior Publication Data
US 2019/0231551 A1    Aug. 1, 2019

Related U.S. Application Data

(60) Provisional application No. 62/384,972, filed on Sep. 8, 2016.

(51) Int. Cl.
*A61F 2/44* (2006.01)
*A61B 17/17* (2006.01)
(Continued)

(52) U.S. Cl.
CPC ........ *A61F 2/4455* (2013.01); *A61B 17/1728* (2013.01); *A61B 17/1757* (2013.01);
(Continued)

(58) Field of Classification Search
CPC .. A61F 2002/30266; A61F 2002/30471; A61F 2002/30538; A61F 2/4455; A61F 2/447
See application file for complete search history.

(56) References Cited

U.S. PATENT DOCUMENTS 5,192,327 A    3/1993 Brantigan
6,835,206 B2    12/2004 Jackson
(Continued)

FOREIGN PATENT DOCUMENTS

WO    99/26562 A1    6/1999

OTHER PUBLICATIONS

International Search Report and Written Opinion from parent PCT/US2017/050775 dated Dec. 26, 2017, 19 pages.
(Continued)

*Primary Examiner* — Samuel S Hanna
(74) *Attorney, Agent, or Firm* — Quarles & Brady LLP

(57) ABSTRACT

A spinal fixation system includes an expandable disc replacement body and an adjustment mechanism. The expandable disc replacement body includes a first wall, a second wall, a hinge connecting the first wall and the second wall, and a first bone-screw receiving section at a proximal end of the first wall. The adjustment mechanism is positioned between the first wall and the second wall, and an angle between the first wall and the second wall can be varied by movement of the adjustment mechanism.

34 Claims, 21 Drawing Sheets

(51) Int. Cl.
  *A61F 2/46* (2006.01)
  *A61B 17/70* (2006.01)
  *A61B 17/80* (2006.01)
  *A61F 2/30* (2006.01)

(52) U.S. Cl.
  CPC ...... *A61B 17/7059* (2013.01); *A61B 17/8009* (2013.01); *A61B 17/8042* (2013.01); *A61F 2/30744* (2013.01); *A61F 2/4611* (2013.01); *A61F 2002/30266* (2013.01); *A61F 2002/30405* (2013.01); *A61F 2002/30471* (2013.01); *A61F 2002/30507* (2013.01); *A61F 2002/30523* (2013.01); *A61F 2002/30538* (2013.01); *A61F 2002/30556* (2013.01); *A61F 2002/30565* (2013.01); *A61F 2002/30578* (2013.01); *A61F 2002/30649* (2013.01); *A61F 2002/449* (2013.01); *A61F 2002/4629* (2013.01)

(56) References Cited

U.S. PATENT DOCUMENTS

| | | |
|---|---|---|
| 8,828,085 B1 | 9/2014 | Jensen |
| 8,845,732 B2 | 9/2014 | Weiman |
| 8,932,355 B2 | 1/2015 | Grotz |
| 8,940,049 B1 | 1/2015 | Jimenez et al. |
| 8,961,607 B2 | 2/2015 | Bucci |
| 9,561,116 B2 | 2/2017 | Weiman |
| 9,566,163 B2 | 2/2017 | Suddaby |
| 9,585,762 B2 | 3/2017 | Suddaby |
| 9,750,618 B1 * | 9/2017 | Daffinson ............... A61F 2/447 |
| 2004/0097935 A1 | 5/2004 | Richelsoph et al. |
| 2004/0102848 A1 | 5/2004 | Michelson |
| 2010/0217336 A1 | 8/2010 | Crawford et al. |
| 2013/0158664 A1 | 6/2013 | Palmatier et al. |
| 2014/0249629 A1 | 9/2014 | Moskowitz et al. |
| 2014/0277489 A1 | 9/2014 | Davenport et al. |
| 2014/0296984 A1 | 10/2014 | Etminan |
| 2015/0057754 A1 | 2/2015 | Reed et al. |
| 2015/0272743 A1 | 10/2015 | Jimenez et al. |
| 2016/0166396 A1 | 6/2016 | McClintock |
| 2017/0086985 A1 * | 3/2017 | McLaughlin ......... A61F 2/4684 |
| 2017/0135824 A1 | 5/2017 | Suddaby |
| 2018/0303621 A1 | 10/2018 | Brotman et al. |

OTHER PUBLICATIONS

K2M, Inc. Mojave PL 3D Expandable Interbody System. Sales Flyer. 2018. 2 pages.

Eisner, Walter, "Medtronic Claims Better Anterior Cervical Fusion System", Orthopedics This Week—ryortho.com, published Oct. 22, 2014. Accessed online at http://ryortho.com/breaking/medtronic-claims-better-anterior-cervical-fusion-system/.

Medtronic Prestige LP Cerivcal Disc System Surgical Technique, 2004.

* cited by examiner

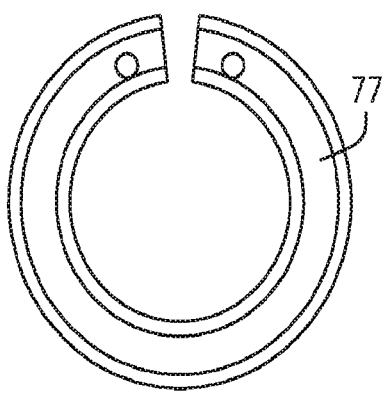
FIG. 6
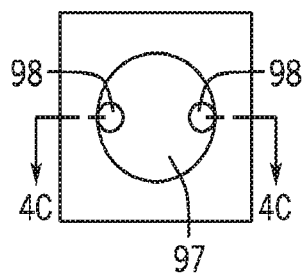
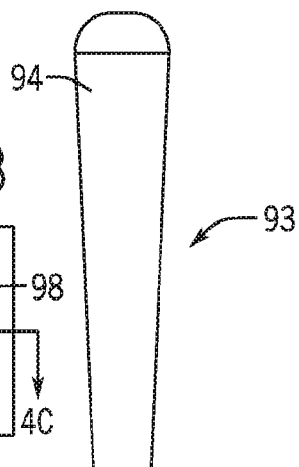
FIG. 4A
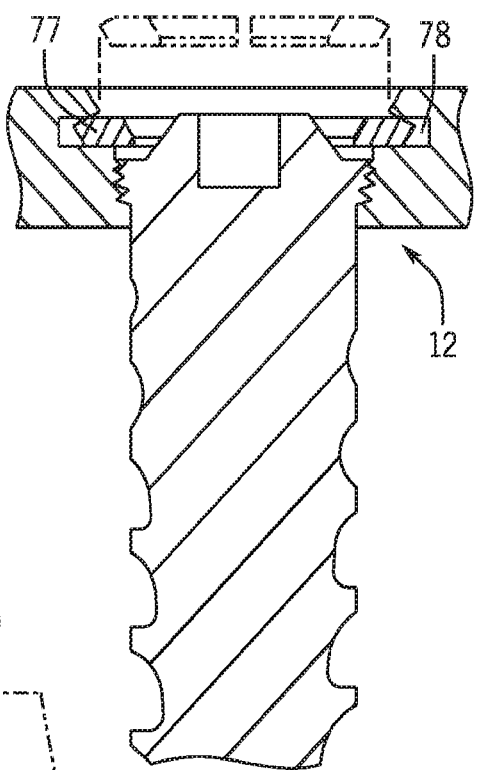
FIG. 5
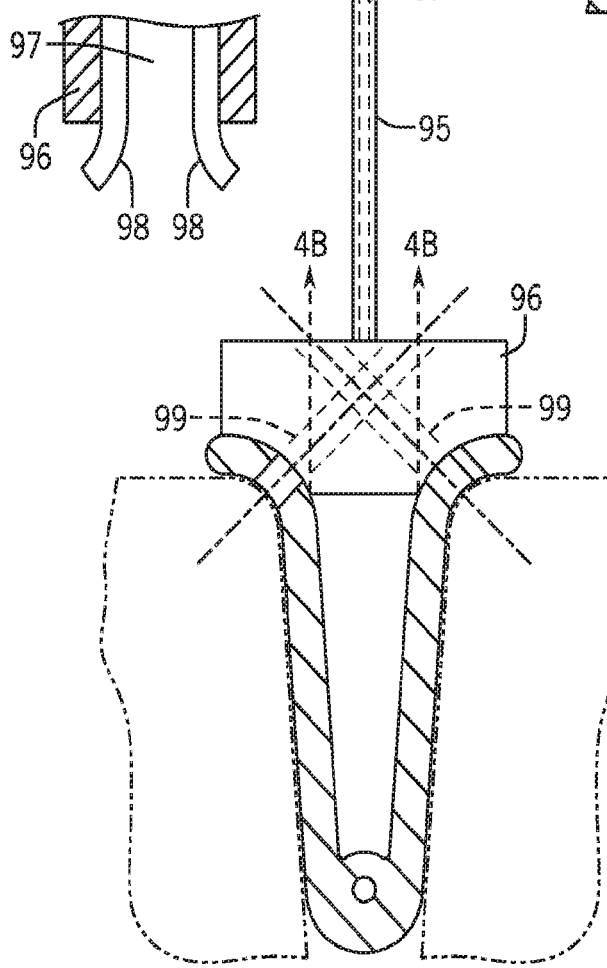

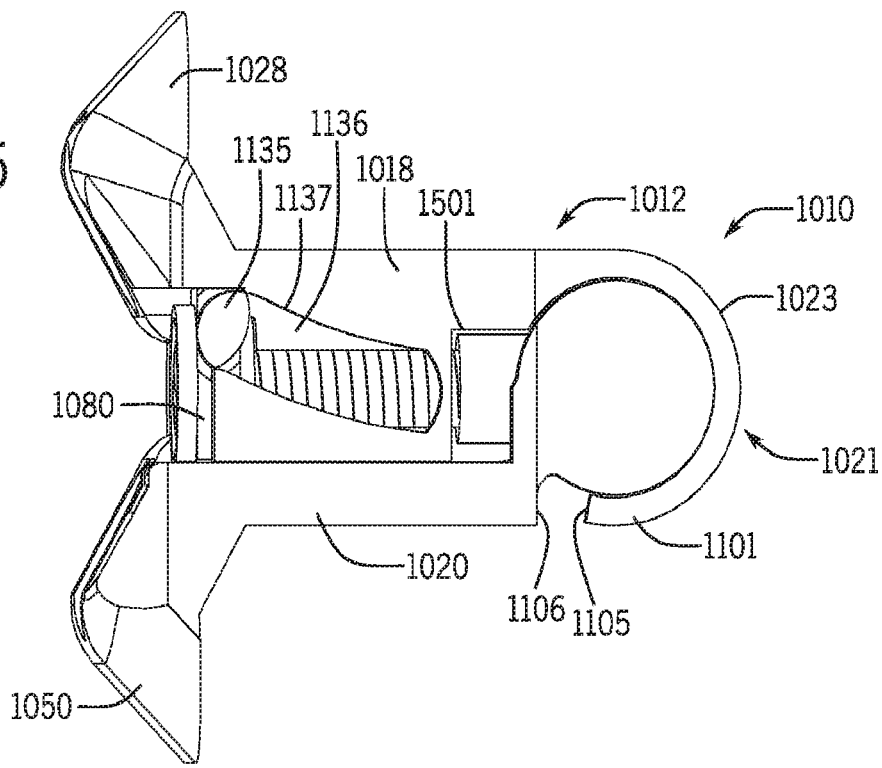
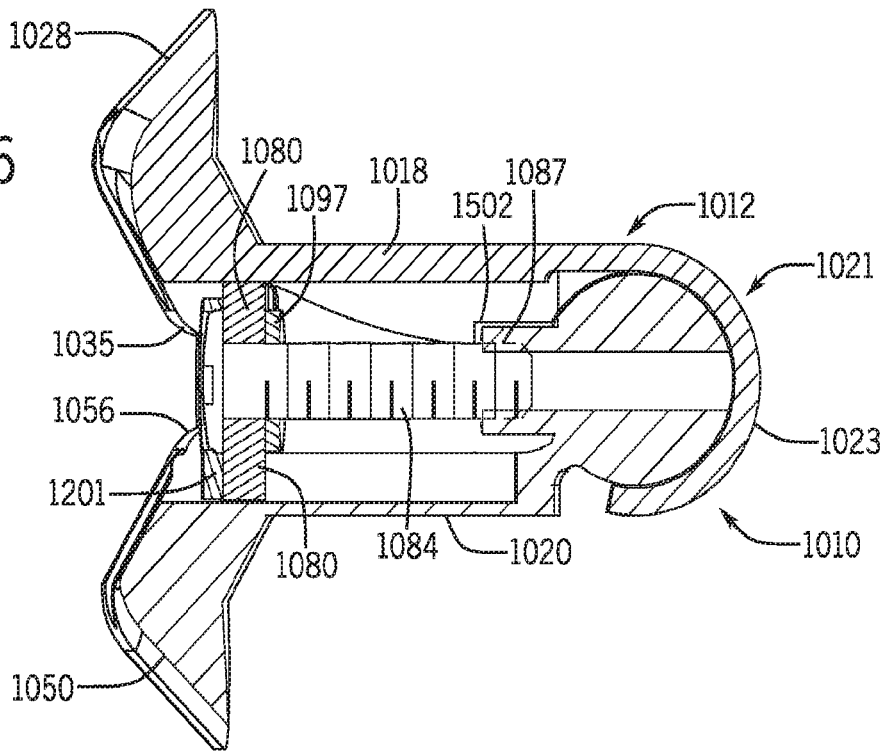

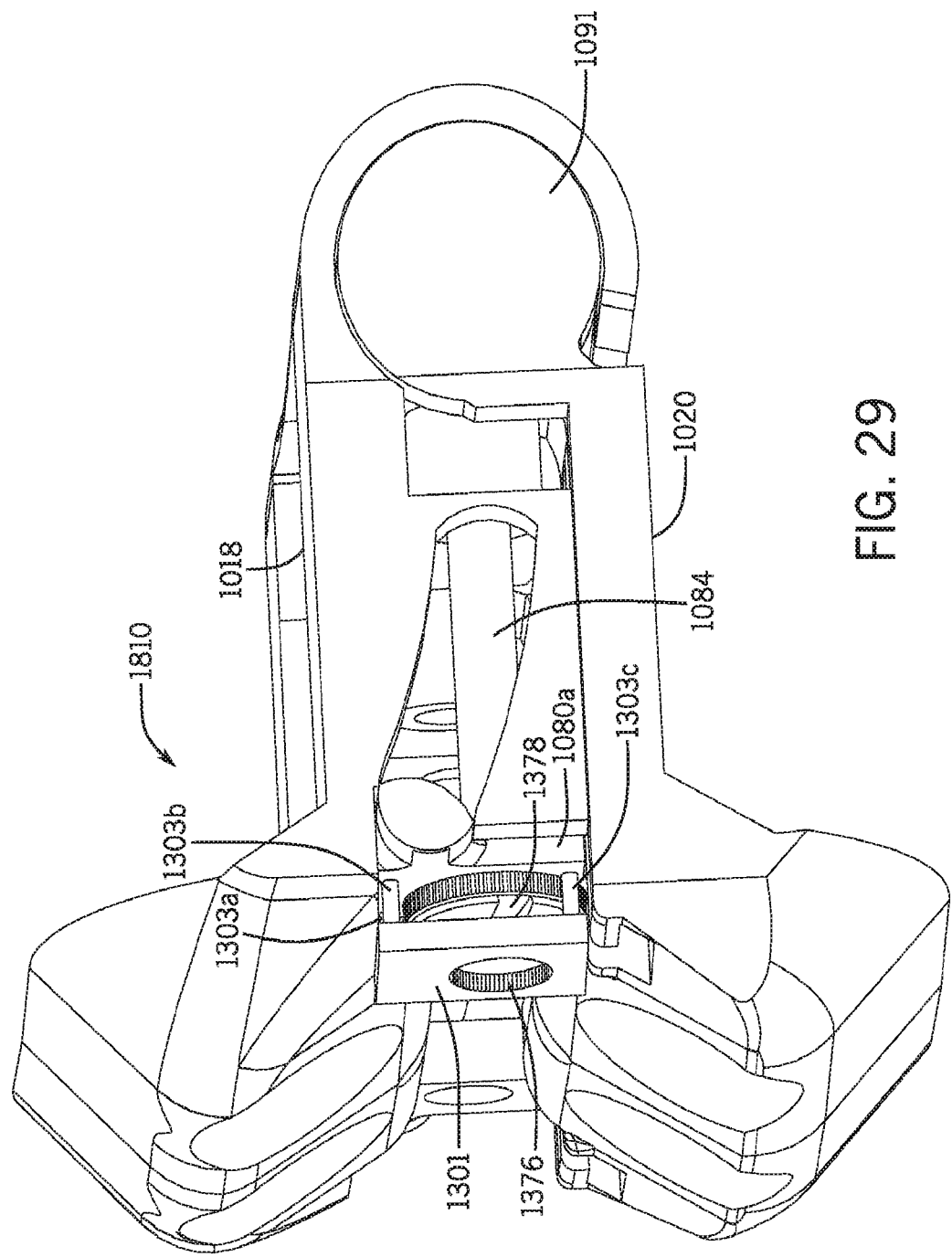

SPINAL FIXATION SYSTEM

CROSS-REFERENCES TO RELATED APPLICATIONS

This application is a 371 U.S. National Phase application of PCT/US17/50775, filed Sep. 8, 2017, which claims priority to U.S. Patent Application No. 62/384,972 filed Sep. 8, 2016.

STATEMENT REGARDING FEDERALLY SPONSORED RESEARCH

Not Applicable.

BACKGROUND OF THE INVENTION

1. Field of the Invention

The invention relates to a fixation system for orthopedic or neurological surgery on a patient, and more particularly to a fixation system for anterior or lateral spine surgery, in which the primary intention is to fuse the spine.

2. Description of the Related Art

As an example, the most common method for surgically decompressing spinal cord or spinal nerve root compression at the level of the cervical spine is a procedure known as an anterior cervical discectomy and fusion. This procedure has been used successfully with minimal change in technique for several decades. Similar anterior and direct lateral approaches to the spine can be used to treat spinal disease at the thoracic, lumbar and lumbo-sacral levels as well. The current standard is that a piece of bone or a cage is placed into the disc space following discectomy, and a plate is then placed over the top of the disc space connecting the bone above and below the disc space via bone screws inserted through openings in the plate. The end goal is to have these two bones grow into one, which is called a fusion. This biological process is significantly enhanced by the rigidity added by the plate fixation and the biological substrate added by the bone or cage (which is filled with bone growth enhancing materials).

Recently, the functions of a plate and a cage have combined in devices that may be called screw-cages. However, these screw-cages provide suboptimal rigidity (especially in weakened bone) and the screws take up space that could be used to achieve a biological fusion. Furthermore, these devices are largely mono-block in nature, which limits their ability to conform to or change the shape of the space in which they are placed as well as preventing the ability to directly compress the bone graft between the endplates of the vertebrae being fused. It is well known to those versed in the art that bone heals best in compression, according to Wolff's Law. Thus, an ideal device would be one that can encourage compression on the graft. Current devices do not possess the ability to directly compress the bone graft between the endplates of the vertebrae being fused.

What is needed therefore is a spinal fixation system that would address these shortcomings.

SUMMARY OF THE INVENTION

The present invention addresses the foregoing needs by providing spinal fixation systems, multi-level spinal fixation systems, and kits for spinal surgery.

In one embodiment, the present disclosure provides a spinal fixation system comprising an expandable disc replacement body including a first wall, a second wall, a hinge connecting the first wall and the second wall; a first bone-screw receiving section at a proximal end of the first wall; and an adjustment mechanism positioned between the first wall and the second wall, wherein an angle between the first wall and the second wall can be continuously varied between a lower value of the angle and an upper value of the angle by movement of the adjustment mechanism. The expandable disc replacement body may include a second bone-screw receiving section at a proximal end of the second wall.

In one aspect of this embodiment, the first bone-screw receiving section has a first opening for receiving a first bone screw, the first opening having a first longitudinal axis, and the first bone-screw receiving section may have a second opening for receiving a second bone screw, the second opening having a second longitudinal axis, and wherein the first longitudinal axis and the second longitudinal axis diverge in a direction toward a distal end of the expandable disc replacement body. The first bone-screw receiving section may have a first recessed edge between the first opening and the second opening. The first bone-screw receiving section may also have a first grasping recess between the first opening and the second opening. The second bone-screw receiving section may have a third opening for receiving a third bone screw, the third opening having a third longitudinal axis, and the second bone-screw receiving section may have a fourth opening for receiving a fourth bone screw, the fourth opening having a fourth longitudinal axis, and wherein the third longitudinal axis and the fourth longitudinal axis diverge in a direction toward a distal end of the expandable disc replacement body.

In another aspect of this embodiment, the adjustment mechanism comprises a first wedge which slidably engages the first and second walls. The first wedge may include a first wedge screw aperture for receiving a first wedge translating screw which is threadably connected to a first internally threaded cylinder that is directly coupled to the hinge of the expandable disc replacement body. The first wedge screw aperture may include a first wedge snap ring recess containing a first wedge snap ring. When the first wedge translating screw is received within the first wedge screw aperture, the first wedge snap ring may expand into the first wedge snap ring recess to allow entry of the first wedge translating screw and if the first wedge translating screw passes the first wedge snap ring, the first wedge snap ring may contract, effectively blocking the first wedge translating screw from backing out.

If the first wedge translating screw is rotated, the rotation may correlate to a predetermined change in the angle between the first and second walls. The adjustment mechanism may further comprise a second wedge which slidably engages the first and second walls. The first wedge and the second wedge may be inserted in unequal amounts to make a first adjustment angle between the first wall and the second wall on one lateral side of the expandable disc replacement body different than a second adjustment angle between the first wall and the second wall on another lateral side of the expandable disc replacement body. An anterior plate cover may be detachably coupled to the proximal end of the first wall. A disc replacement holder including four angled drill guide holes and a grasping mechanism may be detachably coupled to the grasping recess of the first wall.

In yet another aspect of this embodiment, the first opening includes a first snap ring recess containing a first snap ring, and the second opening may include a second snap ring recess containing a second snap ring. When the first bone screw is received within the first opening, the first snap ring may expand into the first snap ring recess to allow entry of the first bone screw and once the first bone screw passes the first snap ring, the first snap ring may contract, effectively blocking the first bone screw from backing out, and when the second bone screw is received within the second opening, the second snap ring may expand into the second snap ring recess to allow entry of the second bone screw and once the second bone screw passes the second snap ring, the second snap ring may contract, effectively blocking the second bone screw from backing out.

Additionally, the third opening may include a third snap ring recess containing a third snap ring, and the fourth opening may include a fourth snap ring recess containing a fourth snap ring. When the third bone screw is received within the third opening, the third snap ring may expand into the third snap ring recess to allow entry of the third bone screw and once the third bone screw passes the third snap ring, the third snap ring may contract, effectively blocking the third bone screw from backing out, and when the fourth bone screw is received within the fourth opening, the fourth snap ring may expand into the fourth snap ring recess to allow entry of the fourth bone screw and once the fourth bone screw passes the fourth snap ring, the fourth snap ring may contract, effectively blocking the fourth bone screw from backing out.

In still another aspect of this embodiment, the first wall has a first space to allow for insertion of bone graft, and the second wall may have a second space to allow for insertion of bone graft. The hinge may be formed by a pliable material coupling the first wall and the second wall. The first wall and the second wall may each include a fixation anchor for engaging a vertebra.

In a further aspect of this embodiment, the adjustment mechanism comprises a scissor jack which engages the first and second walls. The adjustment mechanism may comprise a scissor jack having an anteriorly accessible lead screw, and when the lead screw is rotated, the rotation may correlate to a predetermined change in the angle between the first and second walls. The adjustment mechanism may comprise a scissor jack having a posteriorly accessible lead screw, and when the lead screw is rotated, the rotation may correlate to a predetermined change in the angle between the first and second walls.

In a still further aspect of this embodiment, the adjustment mechanism comprises a feedback device for indicating an increment of movement of the adjustment mechanism. The feedback device may be a tactile device. The feedback device may be a display device. At least one of the first wall and the second wall may include a contoured bone engaging surface. At least one of the first wall and the second wall may include perforations.

In an even further aspect of this design, the hinge comprises a pair of arcuate structures, a pair of cylindrical structures, one of the pair of arcuate structures surrounding one of the pair of cylindrical structures, the other of the pair of arcuate structures surrounding the other of the pair of cylindrical structures, wherein the pair of arcuate structures is connected to at least one of the first wall and the second wall, and wherein the pair of cylindrical structures is connected to the other of the first wall and the second wall. An arcuate length of at least one of the pair of arcuate structures may be used to limit the upper value of the angle by contacting one of the first wall and the second wall. The first wall may have a first space to allow for insertion of bone graft, and the hinge may comprise a bar connecting the pair of arcuate structures or the pair of cylindrical structures. The bar may be convex on a side facing the first space.

The adjustment mechanism may comprise a first wedge which slidably engages the first and second walls, wherein at least one of the first wall and the second wall includes a channel, and wherein the first wedge includes a protrusion which extends into and is movable in the channel. Motion of the first wedge may be along an axis parallel to the second wall.

The adjustment mechanism may comprise a first wedge which slidably engages the first and second walls and a second wedge which slidably engages the first and second walls, wherein one of the first wall and the second wall includes a pair of channels, also wherein the first wedge includes a protrusion which extends into and is movable in one of the pair of channels, and wherein the second wedge includes a protrusion which extends into and is movable in the other of the pair of channels. The first wedge and the second wedge may be located at opposite sides of the first and second walls.

The adjustment mechanism may include at least one threaded fastener in contact with threads in at least one of the first wall, second wall, the hinge, or the first wedge. The adjustment mechanism may comprise a first wedge which slidably engages the first and second walls, wherein the adjustment mechanism includes a threaded fastener threadably connected to an internally threaded hole of one of the pair of cylindrical structures. The adjustment mechanism may include two threaded fasteners which can be inserted in unequal amounts to make a first adjustment angle between the first wall and the second wall on one lateral side of the expandable disc replacement body different than a second adjustment angle between the first wall and the second wall on another lateral side of the expandable disc replacement body.

In another even further aspect of this embodiment, the adjustment mechanism includes a locking component which prevents the adjustment mechanism from changing the angle between the first wall and the second wall when activated. The locking component may comprise a locking bar contacting the expandable disc replacement body which can be inserted into the adjustment mechanism in order to prevent further rotational motion. The locking component may comprise a locking cap contacting the expandable disc replacement body which surrounds the locking mechanism in order to prevent further rotational motion. The locking cap may comprise at least one of teeth, one or more insertable posts, one or more insertable spades, a square cover, a hex cover, or a torx cover for contacting the locking mechanism.

In another embodiment, the present disclosure provides a spinal fixation system comprising a disc replacement body including a first wall and a second wall and a plate including a pair of opposed flanges and a first bone-screw receiving section at a superior end of the plate, wherein the opposed flanges are dimensioned to limit rotational movement of the disc replacement body when the plate is coupled to the disc replacement body. The plate may further include a second bone-screw receiving section at an inferior end of the plate. The first wall and the second wall may be angled such that a first distance between the first wall and the second wall at a proximal end is larger than a second distance between the first wall and the second wall at a distal end. The first wall may have a first space to allow for insertion of bone graft, and the second wall may have a second space to allow for insertion of bone graft.

In one aspect of this embodiment, the first bone-screw receiving section has a first opening for receiving a first bone screw, the first opening having a first longitudinal axis, and the first bone-screw receiving section has a second opening for receiving a second bone screw, the second opening having a second longitudinal axis and the first longitudinal axis, wherein the first longitudinal axis and the second longitudinal axis diverge in a direction toward a distal end of the disc replacement body.

In another aspect of this embodiment, the second bone-screw receiving section has a third opening for receiving a third bone screw, the third opening having a third longitudinal axis, and the second bone-screw receiving section has a fourth opening for receiving a fourth bone screw, the fourth opening having a fourth longitudinal axis, wherein the third longitudinal axis and the fourth longitudinal axis diverge in a direction toward a distal end of the disc replacement body.

In a further aspect of this embodiment the first bone-screw receiving section has a first recessed edge between the first opening and the second opening and the second bone-screw receiving section has a second recessed edge between the third opening and the fourth opening. The plate may be coupled to the disc replacement body by a screw located centrally on the plate such that the plate is coupled to a proximal end of the disc replacement body. The pair of opposed flanges may be movable flanges, such that they can move towards each other and apart from one another. The plate may be coupled to the disc replacement body by the movable flanges of the plate grasping the disc replacement body such that the plate is coupled to a proximal end of the disc replacement body.

In another embodiment, the present disclosure provides a spinal fixation system comprising a disc replacement body portion including a first wall and a second wall, a plate portion including a first bone-screw receiving section at a superior end of the plate portion, and a second bone-screw receiving section at an inferior end of the plate portion, wherein the disc replacement body portion and the plate portion are a unitary component and are comprised of a material continuously forming the disc replacement body portion and the plate portion.

In one aspect of this embodiment, the first bone-screw receiving section has a first opening for receiving a first bone screw, the first opening having a first longitudinal axis, and the first bone-screw receiving section has a second opening for receiving a second bone screw, the second opening having a second longitudinal axis, wherein the first longitudinal axis and the second longitudinal axis diverge in a direction toward a distal end of the disc replacement body portion.

In another aspect of this embodiment, the second bone-screw receiving section has a third opening for receiving a third bone screw, the third opening having a third longitudinal axis, and the second bone-screw receiving section has a fourth opening for receiving a fourth bone screw, the fourth opening having a fourth longitudinal axis, wherein the third longitudinal axis and the fourth longitudinal axis diverge in a direction toward a distal end of the disc replacement body portion.

In a further aspect of this embodiment, the first bone-screw receiving section has a first recessed edge between the first opening and the second opening and the second bone-screw receiving section has a second recessed edge between the third opening and the fourth opening. The first wall may have a first space to allow for insertion of bone graft and the second wall may have a second space to allow for insertion of bone graft. The first wall and the second wall may be angled such that a first distance between the first wall and the second wall at a proximal end is larger than a second distance between the first wall and the second wall at a distal end.

The embodiment may further comprise a wing having a stowed position in which the wing is within a perimeter of the disc replacement body portion and having a deployed position in which the wing extends beyond the perimeter. The embodiment may comprise a second wing having a stowed position in which the second wing is within a perimeter of the disc replacement body portion and having a deployed position in which the second wing extends beyond the perimeter.

In another embodiment, the present disclosure provides a spinal fixation system comprising a disc replacement body including a first wall, a second wall, a joint connecting the first wall and the second wall and an adjustment mechanism positioned between the first wall and the second wall, wherein an angle between the first wall and the second wall can be varied by movement of the adjustment mechanism. The joint may be a ball joint.

In one aspect of this embodiment, the system further comprises a plurality of additional adjustment mechanisms positioned between the first wall and the second wall, wherein an angle between the first wall and the second wall can be varied by movement of each additional adjustment mechanism. The adjustment mechanism and each additional adjustment mechanism may be located at corners of the disc replacement body. The adjustment mechanism and each additional adjustment mechanism may provide multi-planar disc space correction.

In another embodiment, the present disclosure provides a multi-level spinal fixation system comprising a spinal fixation system as described in any of the above embodiments, a second spinal fixation system as described in any of the above embodiments, and a clamp dimensioned to couple together the first spinal fixation system and the second spinal fixation system when the first spinal fixation system and the second spinal fixation system are implanted in different intervertebral disc spaces. In one aspect, the clamp includes an elliptical perimeter and an elongated slot, the clamp spatially fixing the first spinal fixation system relative to the second spinal fixation system.

In another embodiment, the present disclosure provides a kit for spinal surgery comprising a plurality of disc replacement trial components, each of the disc replacement trial components comprising a body including a first wall and a second wall, a plate section including a first bone-screw drill guide section at a superior end of the plate section, and a second bone-screw drill guide section at an inferior end of the plate section, wherein a first body of a first disc replacement trial component of the plurality of disc replacement trial components and a second body of a second disc replacement trial component of the plurality of disc replacement trial components have different exterior dimensions.

In one aspect of this embodiment, the kit comprises a detachable handle configured to engage any of the plurality of disc replacement trial components. A first angle between the first wall and the second wall of the first disc replacement trial component may be different than a second angle between the first wall and the second wall of the second disc replacement trial component.

In another embodiment, the present disclosure provides a method for fixing adjacent vertebrae in a spine comprising obtaining a medical image of the spine, defining native dimensions of a disc space of the spine from the medical image, determining corrected dimensions for the disc space of the spine, inserting a spinal fixation system as described in any of the above embodiments in the disc space of the spine, and adjusting the angle between the first wall and the second wall by movement of the adjustment mechanism such that the disc space of the spine corresponds to the corrected dimensions.

A spinal fixation system of the present disclosure allows a surgeon to affix the cage or bone graft to the plate outside of the body, on the back operating room table, so that the cage and plate can be inserted in a single step, which would save time. In one embodiment, a spinal fixation system of the invention includes means for rigidly affixing the cage or bone graft to the plate, by having a central screw that can be threaded through the plate and into the cage/bone. In an alternative embodiment of the spinal fixation system, a double threaded screw is provided. The double threaded screw includes one thread closing down two transverse projections that pinch the cage/bone into place and a second thread drives into the cage/bone. Cut-outs in the plate allow for placement of distraction pins above and below the plate. Bends in the plate self-center the plate to provide optimal placement of the plate without the need for radiographic guidance. In another embodiment of the spinal fixation system, a jig that is attached during insertion guarantees parallel, well placed screws with a convergent pattern, which is the preferred trajectory.

In another embodiment of the spinal fixation system, the plate/cage device can be placed at multiple levels in a modular fashion, so that each level has its own plate/cage device, instead of the current method of placing one, difficult to fit, plate over the final construct. This also means, that in the 25% of cases that require additional surgery, only one short plate needs to be removed, instead of exposing a long traditional plate.

In another embodiment of the spinal fixation system, there is provided an adjustment mechanism for adjusting the lordosis (i.e., angulation) of the implant in-situ. With the plate-cage in place, one can turn a screw of the adjustment mechanism which then preferentially opens the anterior portion of the plate (and/or cage), which will increase the lordosis. Each turn of the screw a specific number of degrees will provide a set amount of anterior height gain and therefore lordotic angulation (which is trigonometrically determined). Correcting lost lordosis is a key principal in anterior spine surgery and current art fails to achieve this goal.

In another embodiment of the spinal fixation system, an anterior cover plate can be optionally added to the plate system with customizable lordosis, this cover plate can act as a seal to the internal space, so that demineralized bone matrix (DBM), bone chips and/or similar bone growth enhancing material can be contained in the cage. This cover plate can also be thicker to add additional structural support by acting as an anterior riser. This cover plate can snap into place around a flange or can be screwed into place. It can have a central defect that can allow for a syringe to connect to inject DBM or other bone growth stimulating material into the internal space of the cage. This defect can then be covered with a screw. The graft can be placed after the plate has its final lordosis. The graft can slide into place or the graft can be loose paste that is held into place with the cage.

In another embodiment of the spinal fixation system, pre-cut bone grafts can be machined to match the areal dimensions of the central defect in the customizable lordosis plate system, and can be fabricated to different degrees of lordosis and constitutions of cortical vs. cancellous bone to be placed into the central defect as a semi-structural bone graft.

It is an advantage of the invention to provide a modular plate system.

It is another advantage of the invention to provide a modular plate that has the ability to customize lordosis. In-situ lordosis correction as in the present invention is gentler then malleting in hyperlordotic taper cages/grafts. Lordosis is a key sagittal parameter in spinal fusion surgery. Every spinal fusion surgery is a "deformity" surgery. By definition, spinal fusion surgery is intended to permanently eliminate motion at a vertebral motion segment. Thus, every time you eliminate a motion segment, you reduce the spine's ability to compensate for malalignment, especially if that malalignment occurs iatrogenically due to the fusion. Controlled, in-situ lordosis correction, allows for gentle application of corrective force. The device can be inserted in a parallel (planar) fashion, which is relatively small for the space and then the lordosis adjustment mechanism can be engaged, to fill the space and ultimately correct the alignment, thereby improving the sagittal alignment of that segment of the spine. The fact that these adjustments can occur to such a great degree using the same base configuration at any level of the spine, means that a significantly fewer number of devices needed to be present to achieve the same number of final geometric configurations as compared to prior art which utilizes mono-block designs that cannot be in-situ custom corrected. For instance, in the cervical spine, a complete spinal kit could include three basic width-depth dimension sizes that come in five posterior hinge heights. Thus, fifteen total devices would be needed in the kit, but if each device can be custom adjusted, in-situ to 12 degrees of lordosis from a parallel base orientation, then these fifteen devices could replace 180 mono-block devices that would be needed to have the same degree of freedom in terms of final geometric configuration.

It is yet another advantage of the invention to provide a spinal fixation system that includes an adjustable plate/graft or plate/cage interface so that a surgeon can use any company's graft or cage or one that is machined specific for the system.

It is still another a advantage of the invention to provide a spinal fixation system that includes an insertion device which allows for the drill guide and screws to be placed with one instrument, yielding consistent symmetry in screw placement and a one-step insertion of graft and fixation of the plate. In one embodiment, the custom jig for inserting the device, can include a torque-limited, single step screw driver mechanism, that is branched. This allows the surgeon to simultaneously adjust the lordosis producing mechanism located on both sides of the device with a single turn of a screw driver during the insertion step. In other embodiments, the screw driver can be a stand-alone instrument, torque limited to prevent breaking the screw head and/or the vertebral bone.

It is yet another advantage of the invention to provide a spinal fixation system with a plate having an anterior cut-out that allows the plate to be placed with a Caspar pin distractor still in place. As a result, the plate/cage or plate/graft of the invention can be inserted with distraction still being maintained. Many surgeons like the disc space to be distracted when the graft is placed in the traditional method. Use of a Caspar pin distractor (most common method) may not be possible without the anterior cut out of a plate of this embodiment of the spinal fixation system.

It is still another advantage of the invention to provide a spinal fixation system that has a low-profile and short cephalad/caudal extension, but still has definite flanges to prevent over-insertion. This facilitates corner screw placement (strongest bone, better angle of attack) and maximum distance from adjacent levels. An example ideal distance is five millimeters from the adjacent level to minimize risk of adjacent heterotopic ossification. This gives the best chance to place above a prior plate, without need for removal. In one embodiment, the bone screw holes are moved more centrally, to prevent the need for or greatly diminish the length of an anterior flange on one or both sides of the fixation device. This allows for the greatest ability to place this device above an area of the spine which has previously been operated on.

It is yet another advantage of the invention to provide a spinal fixation system with disc replacement trial components that have the corner lips, so they cannot be over inserted into the canal. The disc replacement trial components allow for accurate intraoperative templating of height, length and lordotic angle.

It is still another advantage of the invention to provide a spinal fixation system that has a modular design, that allows for smaller incisions, less magnitude of dissection and retraction. This can facilitate a two (transverse) incision method for long constructs, which may lead to decreased dysphagia.

It is yet another advantage of the invention to provide a spinal fixation system with has a modular design that allows for level-specific lordosis correction. A surgeon can correct some levels more than others.

It is still another advantage of the invention to provide a spinal fixation system that achieves peripheral loading as the weight bearing load on the plate/graft is peripheral, where the bone is strongest.

It is yet another advantage of the invention to provide a spinal fixation system having a one-step insertion handle that allows for fixed angled and locked screw placement. Locking plates are the ideal means for fixating bone with a plate, especially of weakened quality. A locking screw of the spinal fixation system can have threads in the screw head that thread into the plate as they are inserted. This prevents screw stripping as well, since the locking screw threads limit progression of the screw when the screw is fully engaged in the bone. Further, locked screws, make all screws one construct that has to fail simultaneous, as opposed to unlocked screws which can failed individually, since they are not rigidly connected to the plate itself.

It is still another advantage of the invention to provide a spinal fixation system that allows for one-step insertion of the plate/cage or plate graft construct.

It is yet another advantage of the invention to provide a spinal fixation system with an elliptical ring that can be used to connect modular plates in long constructs, where the concern is about the bone quality between plates (i.e., risk of pathologic fracture between two adjacent plates).

It is still another advantage of the invention to provide a spinal fixation system that has the ability to directly compress the graft so that the bones heal in compression.

It is yet another advantage of the invention to provide a spinal fixation system with in-situ, fully customizable lordosis correction (e.g., 12 degrees of angulation).

It is still another advantage of the invention to provide a spinal fixation system wherein each revolution of an adjustment screw equals a selected degree lordosis (e.g., 1 degree) with a palpable click.

It is yet another advantage of the invention to provide a spinal fixation system with a sturdy posterior hinge that sets disc space height (e.g., 5 to 9 millimeters) and has various width/depth sizes (e.g., three sizes).

It is still another advantage of the invention to provide a spinal fixation system that has multiple configurations (e.g., fifteen) allowing for multiple different mono-block equivalents (e.g., one hundred eighty).

It is yet another advantage of the invention to provide a spinal fixation system with custom one-piece insertion instruments.

It is still another advantage of the invention to provide a spinal fixation system with a large central cavity for grafting.

It is yet another advantage of the invention to provide a spinal fixation system with direct compression applied to graft, e.g., anti-kickout flange.

It is still another advantage of the invention to provide a spinal fixation system with an integrated screw-cage construct with low (e.g., 2.8 millimeters) anterior profile only at disc level. A two-part assembly is possible.

It is yet another advantage of the invention to provide a spinal fixation system that facilitates multi-level procedures, e.g., Discectomy-Insert-Screw-Lordose-Graft-Done . . . Next.

It is still another advantage of the invention to provide a spinal fixation system with a vertical anterior overhang (e.g., 4 millimeters)—excellent for adjacent segment degeneration (ASD) with flange-less options possible.

It is yet another advantage of the invention to provide a spinal fixation system with screw purchase in best (not worst) bone (e.g., locking screws).

It is still another advantage of the invention to provide a spinal fixation system with sturdy titanium construction with bone-ingrowth surface, which is an improvement over hydrophobic polyetheretherketone (PEEK) with resultant radiolucencies.

It is yet another advantage of the invention to provide a spinal fixation system with a custom allograft jig, i.e., one ten millimeter bone block can be used for all cases with lordosis cut to exactly match in-situ correction, for ideal endplate effacement. Endplate effacement means that the end plates have good contact with the bone graft and preferably this contact occurs with compression.

It is still another advantage of the invention to provide a spinal fixation system that is useable across the entire spine, both for anterior and lateral entry.

It is yet another advantage of the invention to have a large central cavity that allows for placement of a large piece of bone (allograft or autograft) or bone healing material (like demineralized bone matrix) to be placed in the central portion of the intervertebral place to facilitate fusion. Unlike prior art which has placed the lordosis producing mechanism and/or bone screw fixation holes in or near these locations, thus reducing the space available for successful biological fusion, this invention maximizes the space available for fusion by placing the lordosis producing mechanism on the sides of the device. This improvement over prior art increases the potential for solid bony fusion, which is the successful end-state of a spinal fusion surgery.

It is yet another advantage of the invention to enable the ability to directly compress the bone graft between the endplates of each vertebrae, thus optimizing Wolff's Law. This device can be over-lordosed during the insertion step, to allow for gentle placement of the bone graft material centrally within the device and then the over-lordosis can be reversed and in doing so apply compression to the graft.

It is yet another advantage of the invention that in a preferred embodiment is constructed from metal or metal alloys known to perform well when implanted in vivo. For instance, titanium alloys can be used to fabricate the device and the surfaces of the upper and lower portion of the device that are directly opposed to the vertebral bone can be covered with bone in-growth encouraging preparations, like plasma sprayed particles. This allows for bony integration onto the device, in addition to biological incorporation of the graft placed centrally.

These and other features, aspects, and advantages of the present invention will become better understood upon consideration of the following detailed description, drawings, and appended claims.

BRIEF DESCRIPTION OF THE DRAWINGS

FIG. 4A is similar to the cross-sectional view of the spinal fixation system of FIG. 1 shown in FIG. 2, but further includes a disc replacement holder.

FIG. 4B is a cross-sectional view of the disc replacement holder of FIG. 4A, taken along line 4B-4B of FIG. 4A.

FIG. 4C is a cross-sectional view of the disc replacement holder of FIG. 4A, taken along line 4C-4C of FIG. 4B.

FIG. 5 is an example embodiment of a bone screw received in an opening of a disc replacement body of the spinal fixation system of FIG. 1.

FIG. 6 is a top plan view of a snap ring shown in FIG. 6.

FIG. 25 is a side elevational view of the spinal fixation system of FIG. 22.

FIG. 26 is a cross-sectional view of the spinal fixation system of FIG. 22 taken along line 26-26 of FIG. 22.

FIG. 29 is a front perspective view of a tenth embodiment of a spinal fixation system.

Like reference numerals will be used to refer to like parts from Figure to Figure in the following description of the drawings.

DETAILED DESCRIPTION OF THE INVENTION

Figure 1:
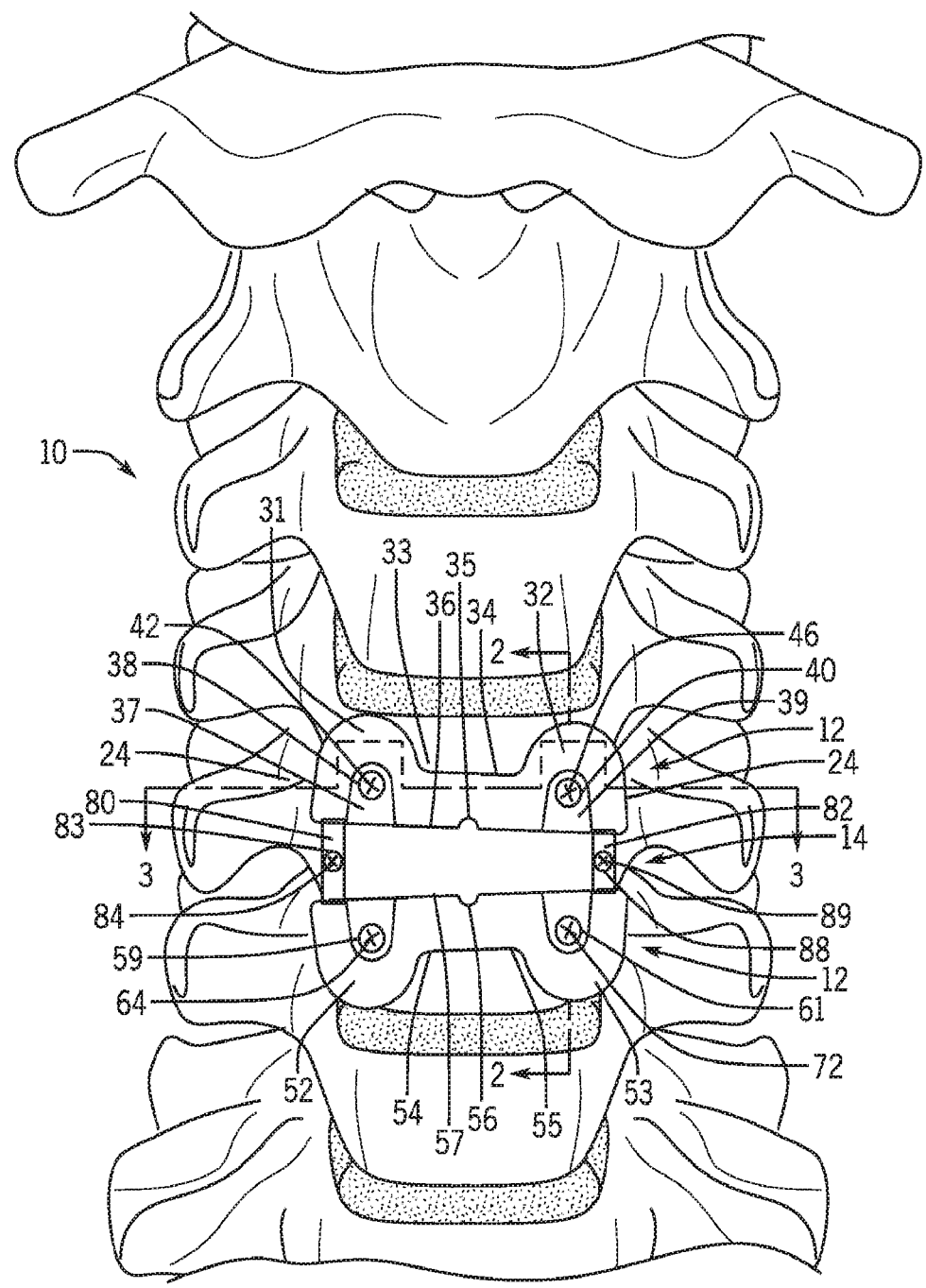
FIG. 1 is a front elevation view of a first embodiment of a spinal fixation system implanted on a spine.
Figure 2:
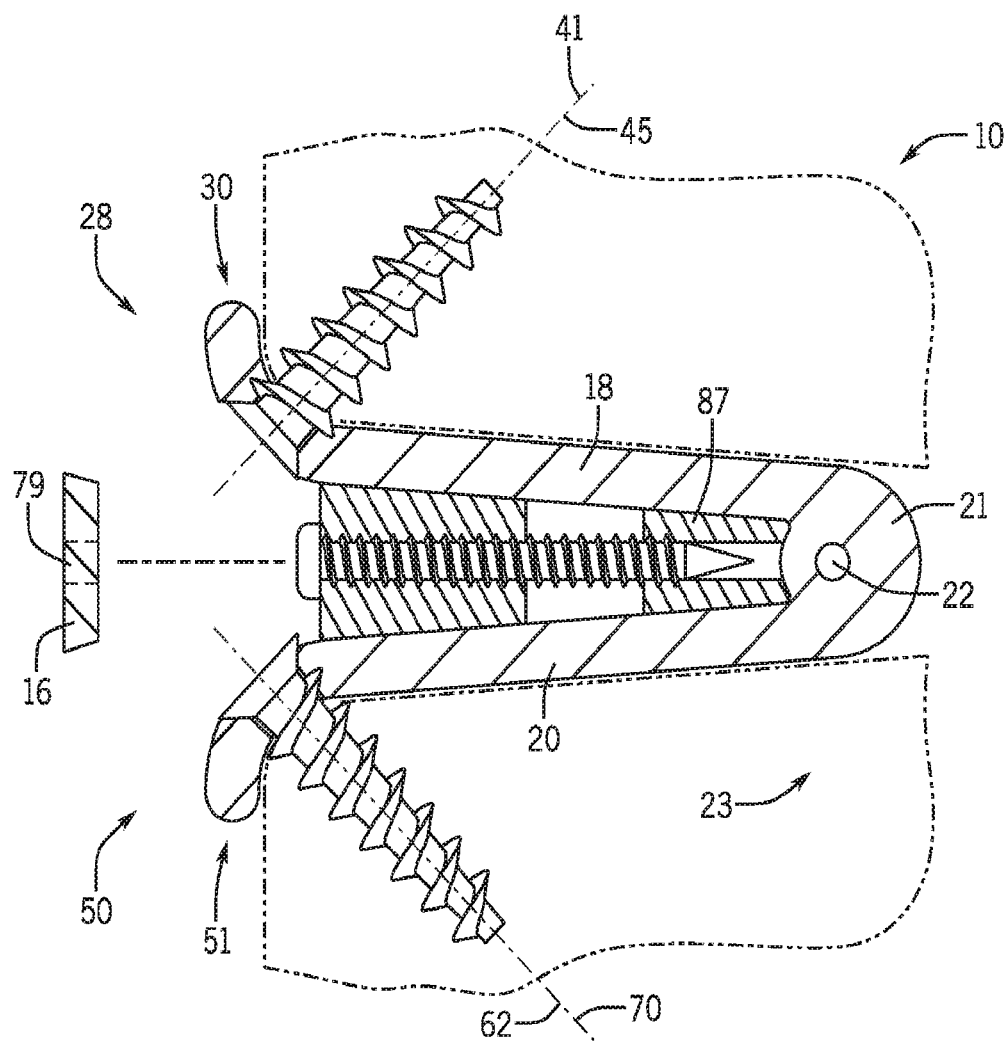
FIG. 2 is a cross-sectional view of the spinal fixation system of FIG. 1, taken along line 2-2 of FIG. 1.
Figure 3:
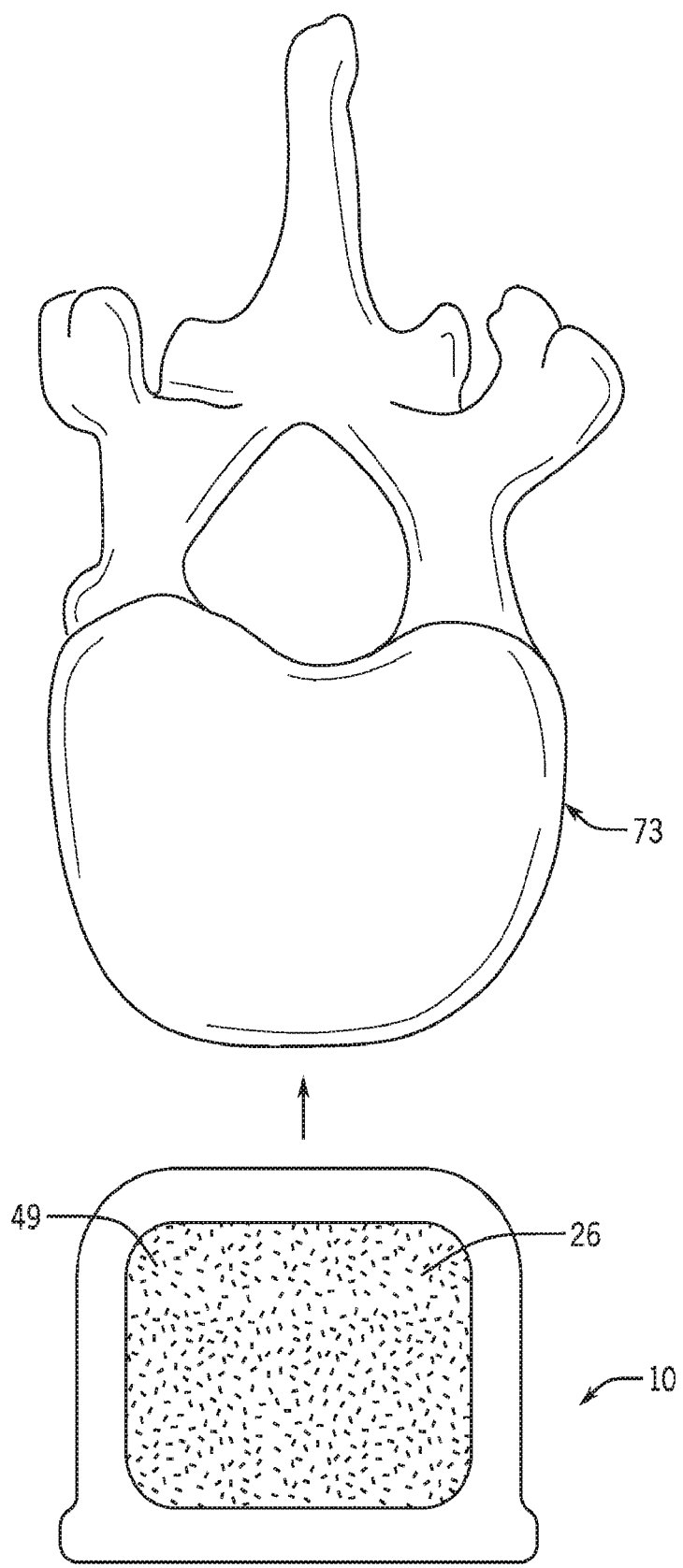
FIG. 3 is a cross-sectional view of the spinal fixation system of FIG. 1, taken along line 3-3 of FIG. 1.
Figure 7:
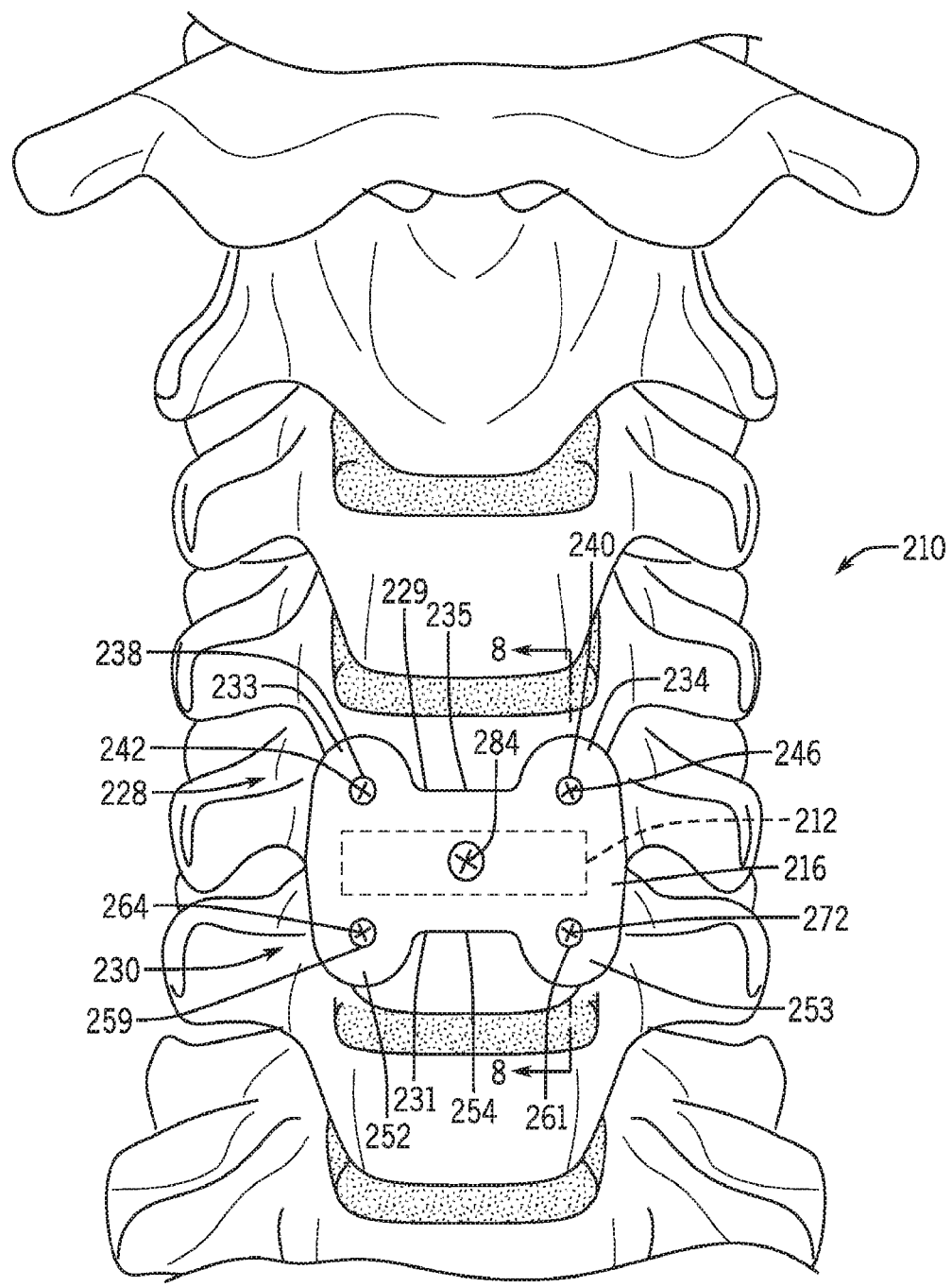
FIG. 7 is a front elevation view of a second embodiment of a spinal fixation system implanted on a spine.
Figure 8:
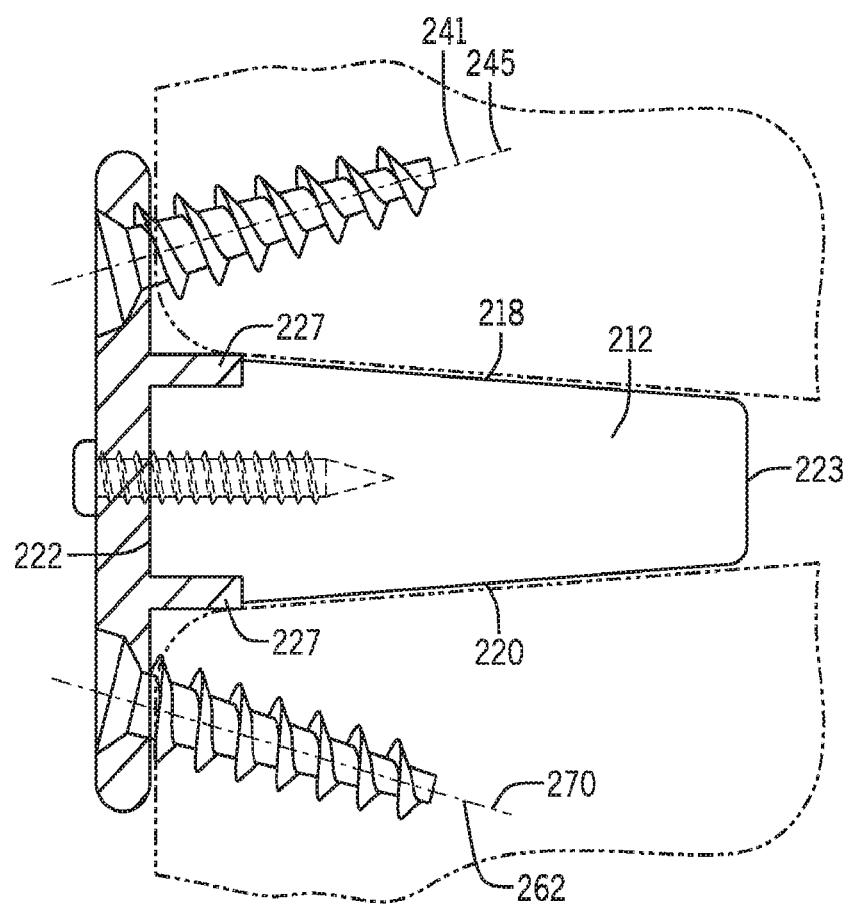
FIG. 8 is a cross-sectional view of the spinal fixation system of FIG. 7, taken along line 8-8 of FIG. 7, shown with a screw coupling a plate to a disc replacement body.
Figure 9:
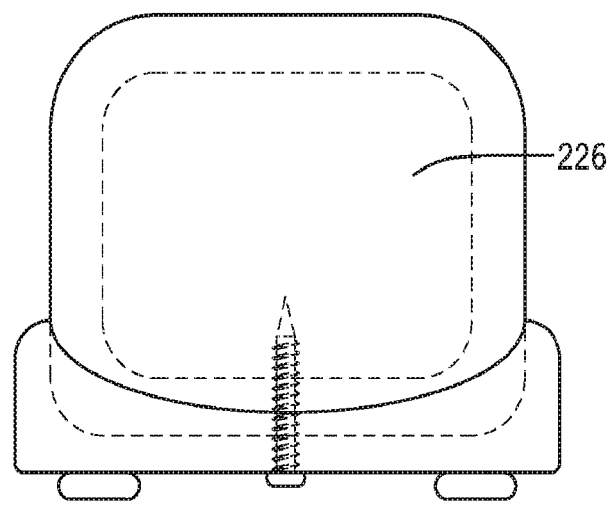
FIG. 9 is a top plan view of the spinal fixation system of FIG. 7.

Turning first to FIGS. 1-6, there is shown a first embodiment of a spinal fixation system 10 according to the invention implanted on a spine. The spinal fixation system 10 includes an expandable disc replacement body 12, an adjustment mechanism 14, and an anterior cover plate 16. The expandable disc replacement body 12 includes a first wall 18, a second wall 20, a hinge 21 including a pin 22 attaching the first wall 18 and the second wall 20 at a distal end 23 of the expandable disc replacement body 12, and two lateral sides 24. The disc replacement body 12 may comprise a metallic material, such as titanium, cobalt chrome or stainless steel, a polymeric material, such as polyetheretherketone, or a ceramic material.

The first wall 18 of the expandable disc replacement body 12 includes a first space 26 for receiving bone graft, such as allograft bone, and a first bone-screw receiving section 28 located on a proximal end 30 of the first wall 18. The first bone-screw receiving section 28 includes a first flange 31, a second flange 32, a first recessed edge 33 located between the first flange 31 and the second flange 32 on a superior edge 34 of the first bone-screw receiving section 28, and a first grasping recess 35 located between the first flange 31 and the second flange 32 on an inferior edge 36 of the first bone-screw receiving section 28. The first bone-screw receiving section 28 may angled back 3-5 degrees from vertical to decrease the profile. The first flange 31 includes a first opening recess 37, which surrounds a first opening 38. The second flange 32 includes a second opening recess 39, which surrounds a second opening 40. The first opening 38 defines a first longitudinal axis 41, and is configured to receive a first bone screw 42, and further includes a first snap ring recess, which is configured to receive a first snap ring. When the first bone screw 42 is received within the first opening 38, the first snap ring expands into the first snap ring recess to allow entry of the first bone screw 42. Once the first bone screw 42 passes the first snap ring, the first snap ring contracts, effectively blocking the first bone screw 42 from backing out. The second opening 40 similarly defines a second longitudinal axis 45, and is configured to receive a second bone screw 46, and further includes a second snap ring recess, which is configured to receive a second snap ring. The second snap ring effectively blocks the second bone screw 46 from backing out in a similar fashion to the first snap ring. The first longitudinal axis 41 and the second longitudinal axis 45 diverge in a direction toward the distal end 23 of the expandable disc replacement body 12.

The second wall 20 of the expandable disc replacement body 12 includes a second space 49 for receiving bone graft, and a second bone-screw receiving section 50 located on a proximal end 51 of the second wall 20. The second bone-screw receiving section 50 may angled back 3-5 degrees from vertical to decrease the profile. The second bone-screw receiving section 50 includes a third flange 52, a fourth flange 53, a second recessed edge 54 located between the third flange 52 and the fourth flange 53 on an inferior edge 55 of the second bone-screw receiving section 50, and a second grasping recess 56 located between the third flange 52 and the fourth flange 53 on a superior edge 57 of the second bone-screw receiving section 50. The third flange 52 includes a third opening recess 58, which surrounds a third opening 59. The fourth flange 53 includes a fourth opening recess 60, which surrounds a fourth opening 61. The third opening 59 defines a third longitudinal axis 62, and is configured to receive a third bone screw 64, and further includes a third snap ring recess, which is configured to receive a third snap ring. The fourth opening 61 defines a fourth longitudinal axis 70, and is configured to receive a fourth bone screw 72, and further includes a fourth snap ring recess, which is configured to receive a fourth snap ring. The third and fourth snap rings effectively block the third and fourth bone screws 64, 72 from backing out in a similar fashion to the first and second snap rings. The third longitudinal axis 62 and the fourth longitudinal axis 70 also diverge in a direction toward the distal end 23 of the expandable disc replacement body 12. The first through fourth snap rings and snap ring recesses described above are identical to a snap ring 77 and a snap ring recess 78 illustrated in FIGS. 5 and 6.

The anterior cover plate 16 can be placed between the first and second walls 18, 20, and may further include grasping notches (not shown) which snap into the first and second grasping recesses 35, 56 of the expandable disc replacement body 12. The anterior cover plate 16 further includes a central defect 79, which can be used to inject bone graft into the interior portion of the expandable disc replacement body 12.

The adjustment mechanism 14 comprises a first wedge 80 and a second wedge 82. The first wedge 80 slidably engages the first wall 18 and the second wall 20 at one of the two lateral sides 24 of the expandable disc replacement body 12, and further includes a first wedge screw aperture 83 configured to receive a first wedge translating screw 84. The first wedge screw aperture 83 further includes a first wedge snap ring recess configured to receive a first wedge snap ring. The first wedge translating screw 84 threadably engages a first internally threaded cylinder 87, which is directly coupled to the hinge 21. The first internally threaded cylinder 87 may include an internal end wall to block further penetration of the screw 84 beyond a position that provides an upper value of the angle (e.g., 12 degrees) between the first wall 18 and the second wall 20.

The second wedge 82 slidably engages the first wall 18 and the second wall 20 at the other of the two lateral sides 24 of the expandable disc replacement body 12, and further includes a second wedge screw aperture 88 configured to receive a second wedge translating screw 89, similar to the first wedge 80. The second wedge screw aperture 88 further includes a second wedge snap ring recess configured to receive a second wedge snap ring. The second wedge translating screw 89 threadably engages a second internally threaded cylinder, similar to the first internally threaded cylinder 87, which is also directly coupled to the hinge 21.

The first and second wedge snap rings and the first and second wedge snap ring recesses described above are identical to the snap ring 77 and snap ring recess 78, shown in FIGS. 5 and 6. The first and second wedge snap rings also effectively block the first and second wedge translating screws from backing out in a similar fashion to the first through fourth snap rings described above.

The spinal fixation system 10 further includes a disc replacement holder 93. The disc replacement holder 93 includes handle 94, a connector shaft 95, and an interface block 96. The disc replacement holder 93 further includes a hollow passageway 97 passing through the handle 94, the connector shaft 95 and the interface block 96, and housing a grasping mechanism 98. The grasping mechanism 98 is configured to grasp the grasping recesses 35, 56 of the first and second bone-screw receiving sections 28, 50 when the grasping mechanism 98 is pushed out of an end of the hollow passageway 97 of the interface block 96. The interface block 96 further includes four angled drill guide holes 99, which may have an inside diameter only slightly larger than the diameter of the bone screw heads.

Now that the structure of the first embodiment of the spinal fixation system 10 has been described, the functionality of the spinal fixation system 10 will be described below.

According to one method of use, in surgery, a surgeon first removes an intervertebral disc from between two adjacent vertebrae of a patient. Then, the expandable disc replacement body 12 of the spinal fixation system 10 described above may be placed between the two adjacent vertebrae, such that the first bone-screw receiving section 28 is adjacent the superior of the two vertebrae and the second bone-screw receiving section 50 is adjacent the inferior of the two vertebrae, which may be done using the disc replacement holder 93. Then, using the four angled drill guide holes 99 on the interface block 96 of the disc replacement holder 93, pilot holes may be drilled into the superior and inferior vertebrae to aid in the insertion of the first through fourth bone screws 42, 46, 64, 72 into the vertebrae. A sounding rod may be inserted thorough the drill guide holes 99 into the pilot holes.

Once the expandable disc replacement body 12 is placed between the two adjacent vertebrae, the first and second bone screws 42, 46 may be screwed into the superior vertebra through the first and second openings 38, 40, respectively, and the third and fourth bone screws 64, 72 may be screwed into the inferior vertebra 73 through the third and fourth openings 59, 61, respectively.

After the first through fourth bone screws 42, 46, 64, 72 are in place, the expandable disc replacement body 12 is effectively locked between the two adjacent vertebrae. At this point, the adjustment mechanism 14 can be used to achieve various angles between the first wall 18 and the second wall 20 of the expandable disc replacement body 12.

As first and second wedge translating screws 84, 89 are rotated clockwise, they force the first and second wedges 80, 82 towards the distal end 23 of the expandable disc replacement body 12, which due to the shape and configuration of the first and second wedges 80, 82 within the first and second walls 18, 20, forces the first and second walls 18, 20 to separate. Because the first and second walls 18, 20 are coupled at the hinge 21, this separation increases an angle formed therebetween. As such, when the first and second wedge translating screws 84, 89 are rotated, the rotation can correlate to a predetermined change in the angle between the first and second walls 18, 20. This capability to change the angle between the first and second walls 18, 20 allows for the expandable disc replacement body 12 to be used to counteract various degrees of lordosis of the spine. The first and second wedge translating screws 84, 89 can include markings on the screw head wherein rotation of the screw head from one marking to the adjacent marking correlates with a predetermined change in the angle between the first and second walls 18, 20. In another non-limiting example embodiment, one degree of opening between the first and second walls 18, 20 can be provided per turn of the screw head.

The first wedge 80 and the second wedge 82 can also be inserted unequal amounts to create a first adjustment angle between the first and second walls 18, 20 on one lateral side 24 of the expandable disc replacement body 12, and a different second adjustment angle between the first and second walls 18, 20 on the other lateral side 24 of the expandable disc replacement body 12. The difference between the first and second adjustment angles may create a slight lateral angle between the first and second walls 18, 20, which may further be used to counteract scoliosis of the spine. In this case, the hinge 21 may alternatively be formed of a pliable material coupling the first and second walls 18, 20 to allow for biaxial rotation.

Referring now to FIGS. 7-9 and 12-13B, there is shown a second embodiment of a spinal fixation system 210 according to the invention implanted on a spine. The spinal fixation system 210 includes a disc replacement body 212 and a plate 216. The disc replacement body 212 includes a first wall 218 and a second wall 220. In some embodiments, the first wall 218 and the second wall 220 can be substantially parallel. In some other embodiments, the first wall 218 and the second wall 220 can be angled such that a first distance between the first wall 218 and the second wall 220 at a proximal end 222 of the disc replacement body 212 is larger than a second distance between the first wall 218 and the second wall 220 at a distal end 223 of the disc replacement body 212. The first wall 218 and the second wall 220 further include a bone graft chamber 226 formed therebetween and capable of receiving bone graft.

The plate 216 includes a pair of opposed flanges 227, a first bone-screw receiving section 228 at a superior edge 229 of the plate 216, and a second bone-screw receiving section 230 at an inferior edge 231 of the plate 216. When the spinal fixation system 210 is assembled, the plate 216 and the disc replacement body 212 are coupled together and the pair of opposed flanges 227 engage the first and second walls 218, 220 of the disc replacement body 212, effectively limiting rotational motion of the disc replacement body 212. The first bone-screw receiving section 228 includes a first flange 233, a second flange 234, and a first recessed edge 235 located between the first flange 233 and the second flange 234 on the superior edge 229 of the plate 216. The first flange 233 and the second flange 234 include a first opening 238 and a second opening 240, respectively. The first opening 238 defines a first longitudinal axis 241, is configured to receive a first bone screw 242, and may further include a first snap ring recess, which is configured to receive a first snap ring, as shown in FIGS. 5 and 6. In this case, when the first bone screw 242 is received within the first opening 238, the first snap ring expands into the first snap ring recess to allow entry of the first bone screw 242. Once the first bone screw 242 passes the first snap ring, the first snap ring contracts, effectively blocking the first bone screw 242 from backing out. The second opening 240 similarly defines a second longitudinal axis 245, is configured to receive a second bone screw 246, and may further include a second snap ring recess, which is configured to receive a second snap ring, as shown in FIGS. 5 and 6. Again, in this case, the second snap ring effectively blocks the second bone screw 246 from backing out in a similar fashion to the first snap ring. The first longitudinal axis 241 and the second longitudinal axis 245 diverge in a direction toward the distal end 223 of the disc replacement body 212.

The second bone-screw receiving section 230 includes a third flange 252, a fourth flange 253, and a second recessed edge 254 located between the third flange 252 and the fourth flange 253 on the inferior edge 231 of the plate 216. The third flange 252 and the fourth flange 253 include a third opening 259 and a fourth opening 261, respectively. The third opening 259 defines a third longitudinal axis 262, is configured to receive a third bone screw 264, and may further includes a third snap ring recess, which is configured to receive a third snap ring, as shown in FIGS. 5 and 6. The fourth opening 261 defines a fourth longitudinal axis 270, is configured to receive a fourth bone screw 272, and may further include a fourth snap ring recess, which is configured to receive a fourth snap ring, as shown in FIGS. 5 and 6. The third and fourth snap rings effectively block the third and fourth bone screws 264, 272 from backing out in a similar fashion to the first and second snap rings. The third longitudinal axis 262 and the fourth longitudinal axis 270 also diverge in a direction toward the distal end 223 of the disc replacement body 212.

Figure 13A:
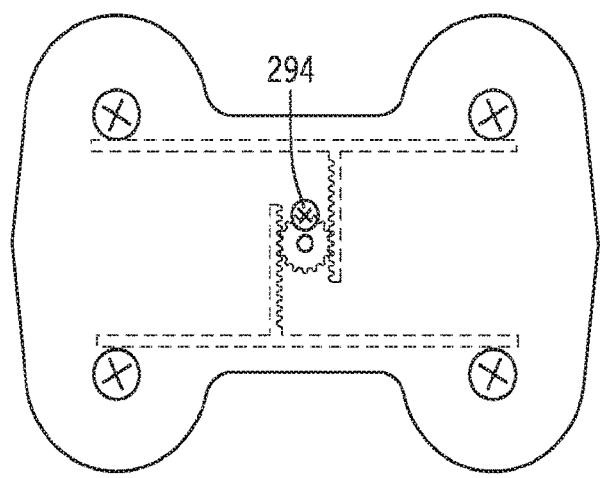
FIG. 13A is a front elevation view of the spinal fixation system of FIG. 7, shown with a rack and pinion system in dashed lines.
Figure 13B:
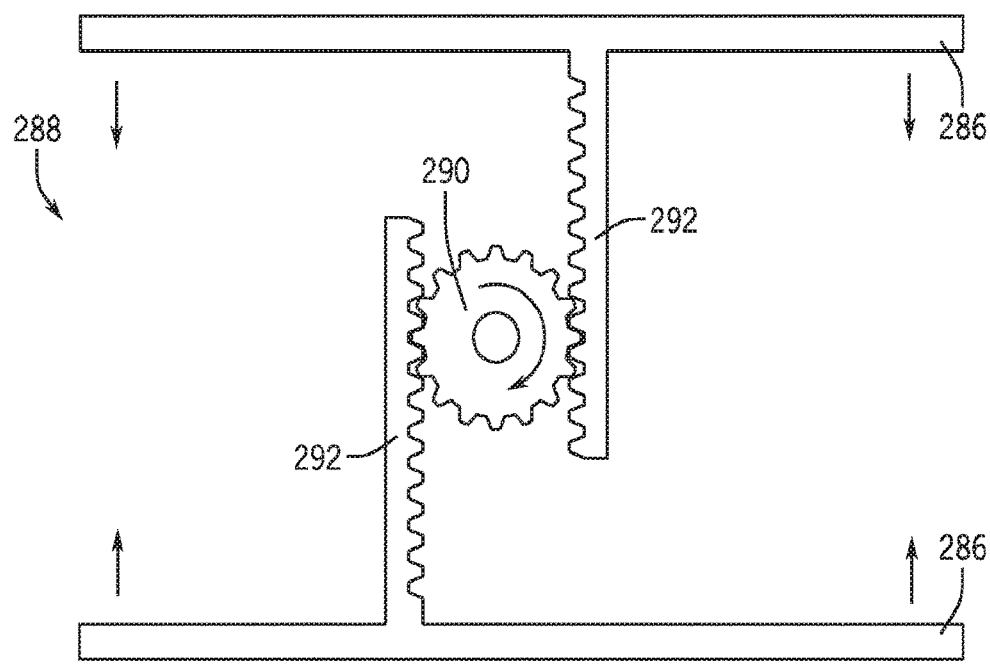
FIG. 13B is a detail view of the rack and pinion system of FIG. 13A.

The disc replacement body 212 and the plate 216 of the spinal fixation system 210 can be coupled in a multitude of methods. In some embodiments, the disc replacement body 212 can be coupled to the plate 216 using a screw 284 located centrally on the plate 216 such that the plate 216 is coupled to the proximal end 222 of the disc replacement body 212. In some other embodiments, the pair of opposed flanges 227 can be a pair of opposed moveable flanges 286, such that they can move towards each other and apart from one another, as shown in FIGS. 13A and 13B. In this case, the pair of opposed moveable flanges 286 can move together to grasp the disc replacement body 212 such that the plate 216 is coupled to the proximal end 222 of the disc replacement body 212.

As shown in FIGS. 13A and 13B, the pair of opposed moveable flanges 286 can be moveable using a rack and pinion adjustment mechanism 288. Using the rack and pinion adjustment mechanism 288, a central gear 290 can be rotated to force a pair of gear toothed bars 292, which are coupled to the pair of opposed moveable flanges 286, to move relative to each other. As the pair of gear toothed bars 292 move relative to each other, the pair of opposed moveable flanges 286 can move towards each other or apart from each other. Once the pair of opposed moveable flanges 286 are in a desired position, they can be locked in place using a set screw 294.

Now that the structure of the second embodiment of the spinal fixation system 210 has been described, the functionality of the spinal fixation system 210 will be described below.

According to one method of use, the spinal fixation system 210 is assembled prior to surgery, such that the plate 216 is coupled to the proximal end 222 of the disc replacement body 212. Then, during surgery, a surgeon first removes an intervertebral disc from between two adjacent vertebrae of a patient. Then, the disc replacement body 212 of the spinal fixation system 210 described above may be placed between the two adjacent vertebrae, such that the first bone-screw receiving section 228 of the plate 216 is adjacent the superior of the two vertebrae and the second bone-screw receiving section 230 is adjacent the inferior of the two vertebrae.

Once the disc replacement body 212 is placed between the two adjacent vertebra, the first and second bone screws 242, 246 may be screwed into the superior vertebra through the first and second openings 238, 240, respectively, and the third and fourth bone screws 264, 272 may be screwed into the inferior vertebra through the third and fourth openings 259, 261, respectively.

After the first through fourth bone screws, 242, 246, 264, 272 are in place, the disc replacement body 212 is effectively locked between the two adjacent vertebrae.

Alternatively, the plate 216 can be coupled to the proximal end 222 of the disc replacement body 212 after the disc replacement body 212 is placed between the two adjacent vertebrae.

Figure 10A:
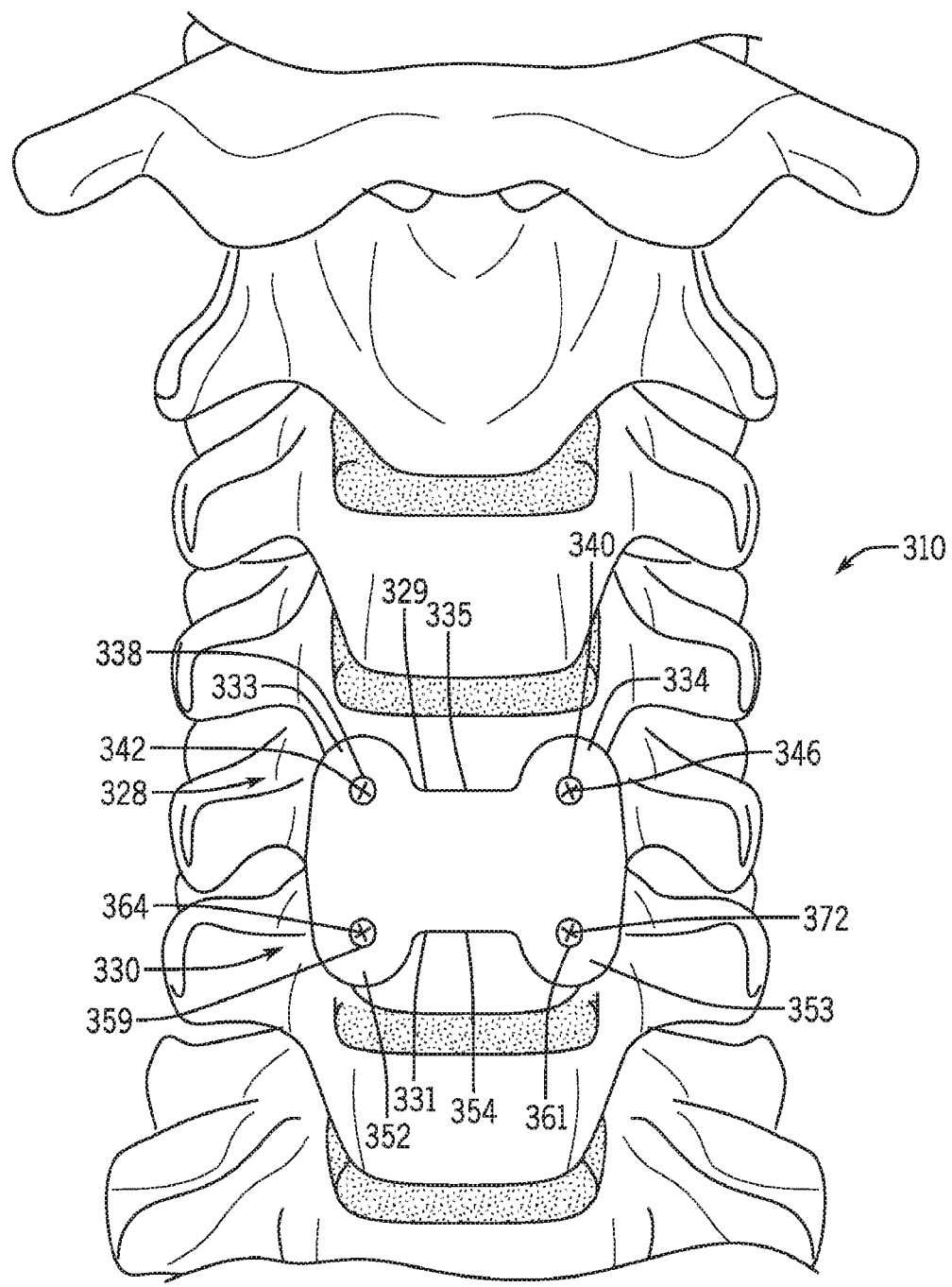
FIG. 10A is a front elevation view of a third embodiment of a spinal fixation system implanted on a spine.
Figure 10B:
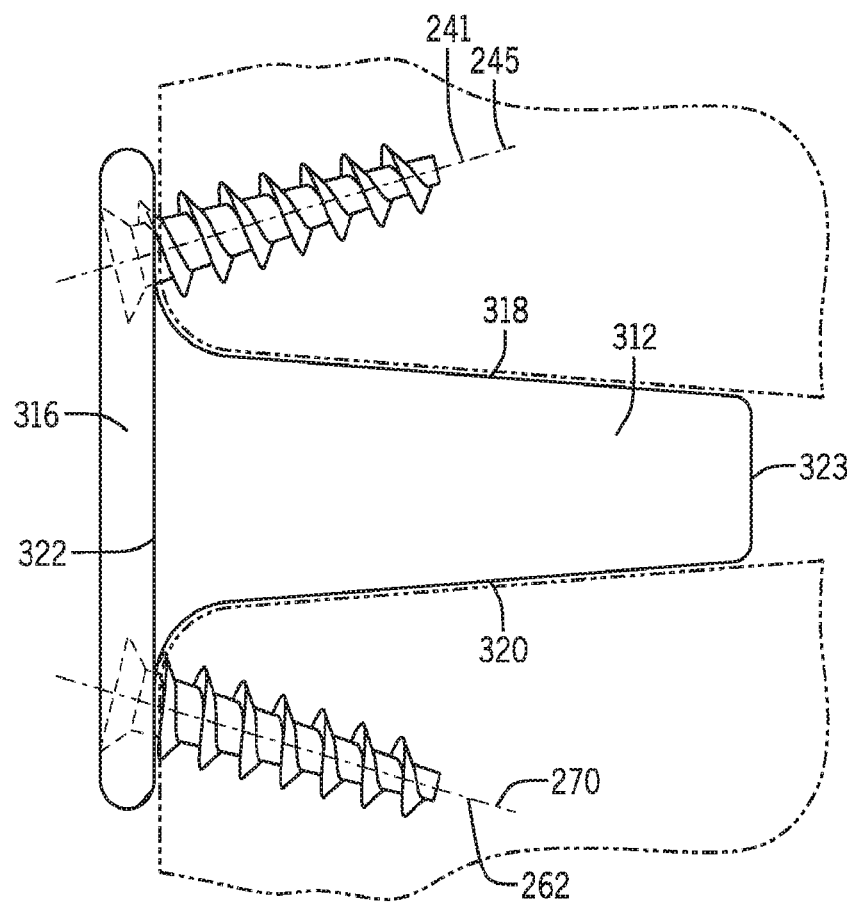
FIG. 10B is a side elevation view of the spinal fixation system of FIG. 10A.
Figure 11:
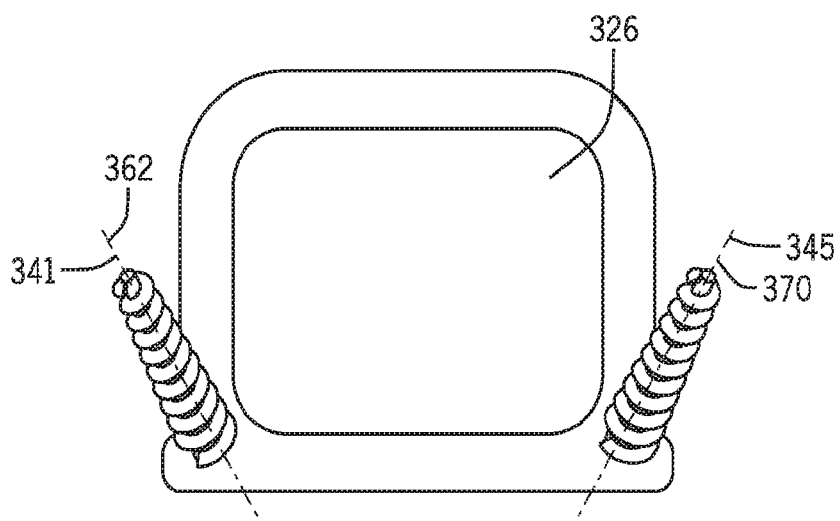
FIG. 11 is a top plan view of the spinal fixation system of FIG. 10A.
Figure 12:
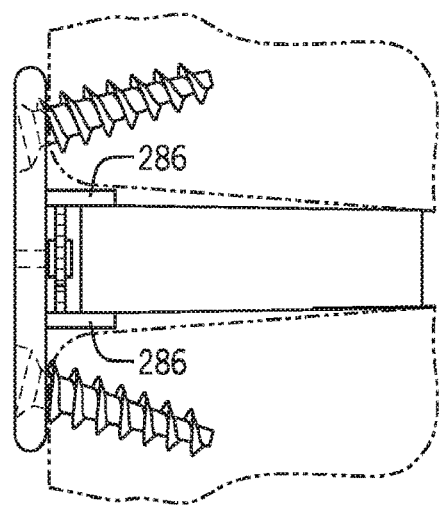
FIG. 12 is a side elevation view of the spinal fixation system of FIG. 7, shown with a pair of movable flanges coupling a plate to a disc replacement body.

Turning now to FIGS. 10A-11, there is shown a third embodiment of a spinal fixation system 310 according to the invention implanted on a spine. The spinal fixation system 310 includes a disc replacement body portion 312 and a plate portion 316. The disc replacement body portion 312 and the plate portion 316 are a unitary component and are comprised of a material continuously forming the disc replacement body portion 312 and the plate portion 316. Said differently, the disc replacement body portion 312 and the plate portion 316 are a unitary component, such that the entire unitary component may be molded, cast, or otherwise formed in a single piece, with no assembly required. The disc replacement body portion 312 includes a first wall 318 and a second wall 320. In some embodiments, the first wall 318 and the second wall 320 can be substantially parallel. In some other embodiments, the first wall 318 and the second wall 320 can be angled such that a first distance between the first wall 318 and the second wall 320 at a proximal end 322 of the disc replacement body portion 312 is larger than a second distance between the first wall 318 and the second wall 320 at a distal end 323 of the disc replacement body portion 312. The first wall 318 and the second wall 320 further include a bone graft chamber 326 formed therebetween and capable of receiving bone graft.

The plate portion 316 includes a first bone-screw receiving section 328 at a superior edge 329 of the plate portion 316, and a second bone-screw receiving section 330 at an inferior edge 331 of the plate portion 316. The first bone-screw receiving section 328 includes a first flange 333, a second flange 334, and a first recessed edge 335 located between the first flange 333 and the second flange 334 on the superior edge 329 of the plate portion 316. The first flange 333 and the second flange 334 include a first opening 338 and a second opening 340, respectively. The first opening 338 defines a first longitudinal axis 341, is configured to receive a first bone screw 342, and may further include a first snap ring recess, which is configured to receive a first snap ring, as shown in FIGS. 5 and 6. When the first bone screw 342 is received within the first opening 338, the first snap ring expands into the first snap ring recess to allow entry of the first bone screw 342. Once the first bone screw 342 passes the first snap ring, the first snap ring contracts, effectively blocking the first bone screw 342 from backing out. The second opening 340 similarly defines a second longitudinal axis 345, is configured to receive a second bone screw 346, and may further include a second snap ring recess, which is configured to receive a second snap ring, as shown in FIGS. 5 and 6. The second snap ring effectively blocks the second bone screw 346 from backing out in a similar fashion to the first snap ring. The first longitudinal axis 341 and the second longitudinal axis 345 diverge in a direction toward the distal end 323 of the disc replacement body portion 312.

The second bone-screw receiving section 330 includes a third flange 352, a fourth flange 353, and a second recessed edge 354 located between the third flange 352 and the fourth flange 353 on the inferior edge 331 of the plate portion 316. The third flange 352 and the fourth flange 353 include a third opening 359 and a fourth opening 361, respectively. The third opening 359 defines a third longitudinal axis 362, is configured to receive a third bone screw 364, and may further include a third snap ring recess, which is configured to receive a third snap ring, as shown in FIGS. 5 and 6. The fourth opening 361 defines a fourth longitudinal axis 370, is configured to receive a fourth bone screw 372, and may further include a fourth snap ring recess, which is configured to receive a fourth snap ring, as shown in FIGS. 5 and 6. The third and fourth snap rings effectively block the third and fourth bone screws 364, 372 from backing out in a similar fashion to the first and second snap rings. The third longitudinal axis 362 and the fourth longitudinal axis 370 also diverge in a direction toward the distal end 323 of the disc replacement body portion 312.

Having described the structure of the third embodiment of the spinal fixation system 310, the functionality of the spinal fixation system 310 will be described below.

According to one method of use, in surgery, a surgeon first removes an intervertebral disc from between two adjacent vertebrae of a patient. Then, the disc replacement body portion 312 of the spinal fixation system 310 described above may be placed between the two adjacent vertebrae, such that the first bone-screw receiving section 328 is adjacent the superior of the two vertebrae and the second bone-screw receiving section 330 is adjacent the inferior of the two vertebrae.

Once the disc replacement body portion 312 is placed between the two adjacent vertebrae, the first and second bone screws 342, 346 may be screwed into the superior vertebra through the first and second openings 338, 340, respectively, and the third and fourth bone screws 364, 372 may be screwed into the inferior vertebra through the third and fourth openings 359, 361, respectively.

After the first through fourth bone screws, 342, 346, 364, 372 are in place, the disc replacement body portion 312 is effectively locked between the two adjacent vertebrae.

Figure 14:
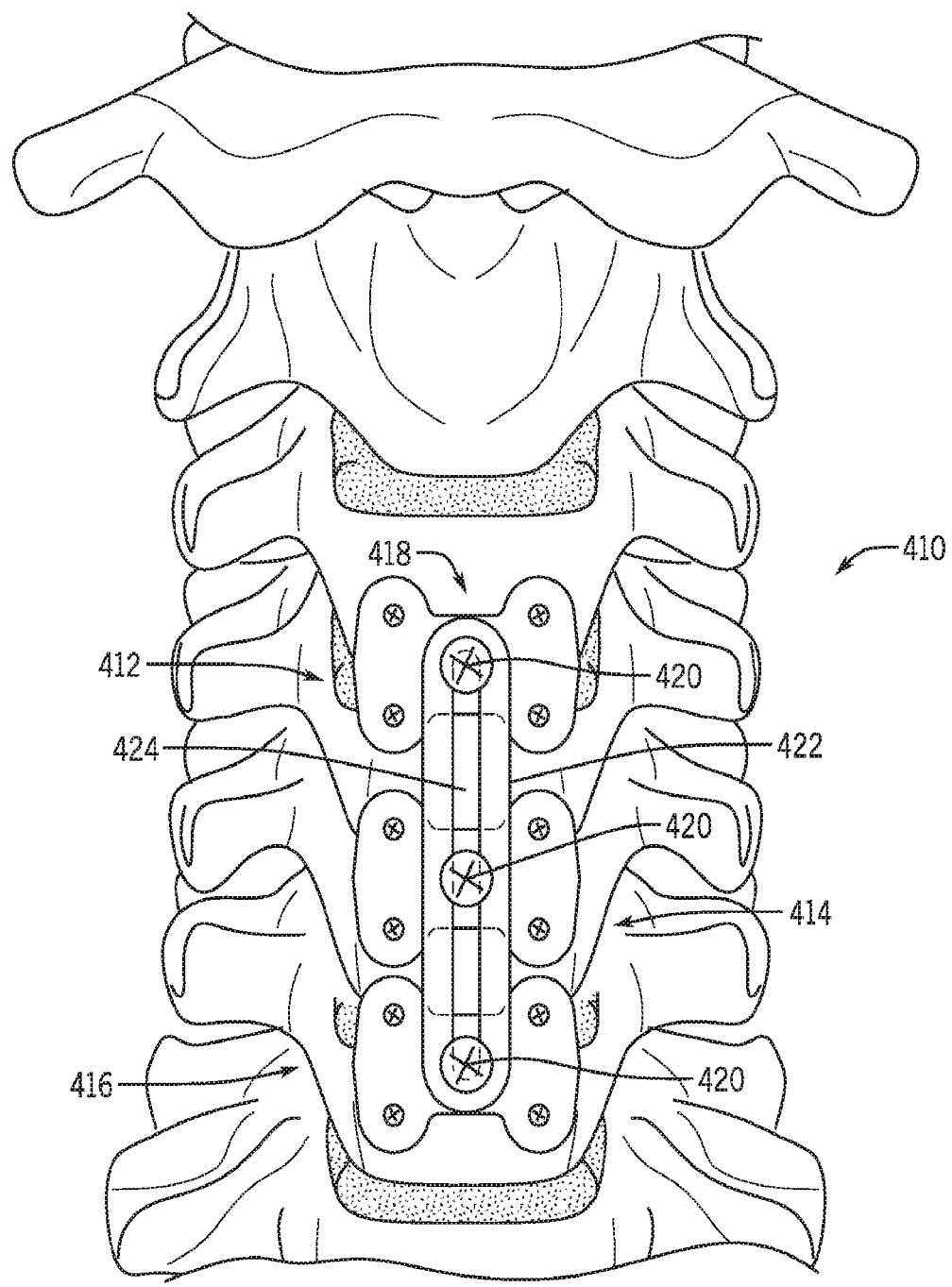
FIG. 14 is a front elevation view of a multi-level spinal fixation system implanted on a spine.

Referring now to FIG. 14, there is shown a multi-level spinal fixation system 410 according to the invention implanted on a spine. The multi-level spinal fixation system 410 includes a first spinal fixation system 412, a second spinal fixation system 414, a third spinal fixation system 416, and a clamp 418 dimensioned to couple together the first, second, and third spinal fixation systems 412, 414, 416 when the first, second, and third spinal fixation systems 412, 414, 416 are implanted in different intervertebral disc spaces. Each of the first, second, and third spinal fixation systems 412, 414, 416 can be any of the previously described embodiments (corresponding to spinal fixation system 10, spinal fixation system 210, or spinal fixation system 310) or can be any other spinal fixation systems that may be used during spinal disc replacement surgery. Each of the first, second and third spinal fixation systems 412, 414, 416 further include a fixing element 420. The clamp 418 includes an elliptical perimeter 422 and an elongated slot 424, configured to receive the fixing elements 420 of the first, second, and third spinal fixation systems 412, 414, 416. The clamp 418 may have a backout flange.

According to one method of use, in surgery, a surgeon would first remove the intervertebral discs from between multiple pairs of adjacent vertebrae of a patient. Then, any of the disc replacement bodies or body portions 12, 212, 312 of any of the spinal fixation systems 10, 210, 310 described above may be placed between the multiple pairs of adjacent vertebrae, effectively replacing the intervertebral discs. Once the spinal fixation systems 10, 210, 310 are between the multiple pairs of adjacent vertebrae of the patient, they are screwed into the multiple pairs of adjacent vertebrae, using bone screws, as described above.

After the bone screws are in place, the spinal fixation systems 10, 210, 310 are effectively locked between the multiple pairs of adjacent vertebrae. The fixing elements 420 can then be coupled together by the clamp 418. At this point the fixing elements 420 are received within the elongated slot 424 of the clamp 418, such that they are spatially fixed relative to each other.

Figure 15:
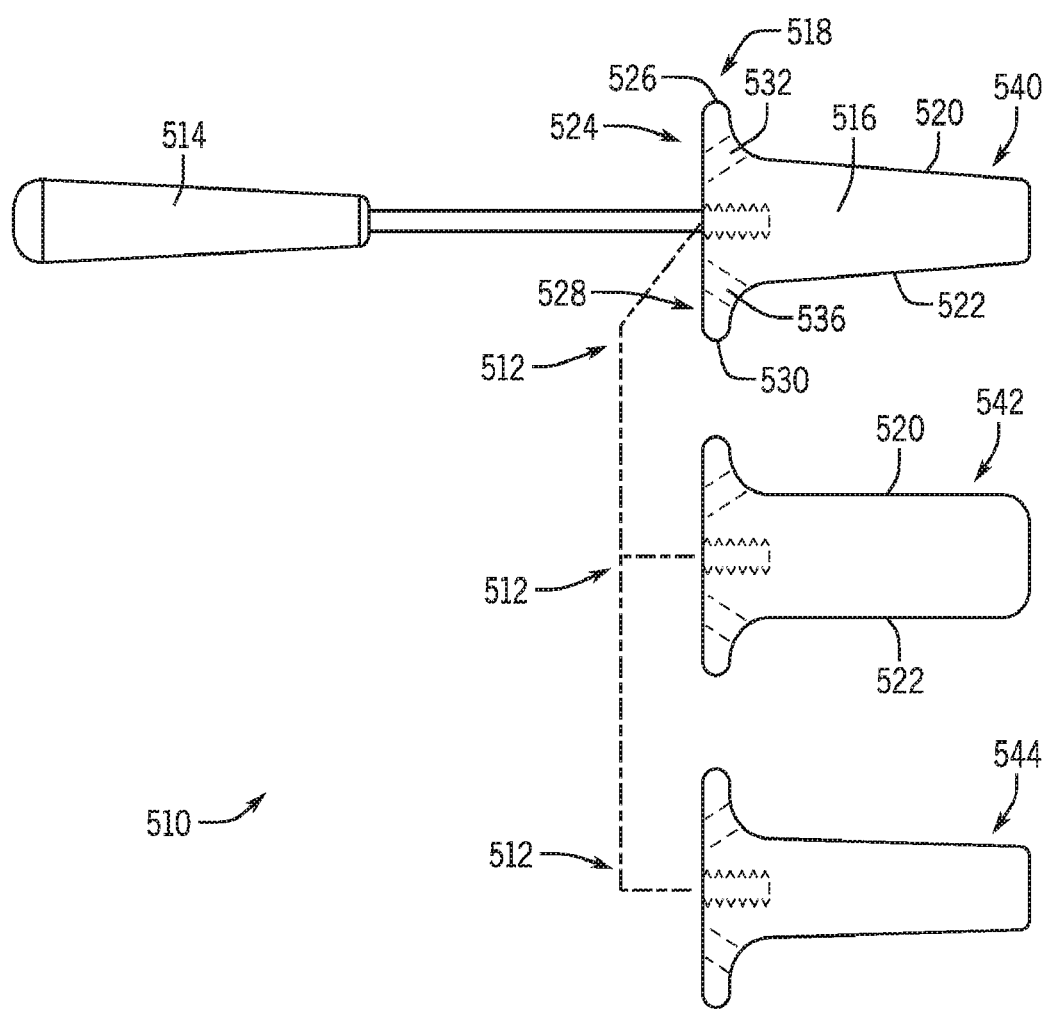
FIG. 15 is a side elevation view of a kit for spinal surgery.

Turning now to FIG. 15, there is shown a kit 510 for determining an appropriate sized disc replacement body for spinal surgery according to the invention. The kit 510 comprises a plurality of disc replacement trial components 512 and a detachable handle 514 configured to removably engage any of the plurality of disc replacement trial components 512.

Each of the plurality of disc replacement trial components 512 have different exterior dimensions and comprise a body 516 and a plate section 518. Each body 516 further includes a first wall 520 and a second wall 522. Each plate section 518 further includes a first bone-screw drill guide section 524 at a superior end 526 of the plate section 518 and a second bone-screw drill guide section 528 at an inferior end 530 of the plate section 518. The first bone-screw drill guide section 524 includes two first bone-screw drill guide section holes 532. Similarly, the second bone-screw drill guide section 528 includes two second bone-screw drill guide section holes 536.

The plurality of disc replacement trial components 512 further includes a first disc replacement trial component 540, a second disc replacement trial component 542, and a third disc replacement trial component 544. Although in the illustrated embodiment, there are three disc replacement trial components 512, in other embodiments there can be two or more disc replacement trial components 512.

In some instances, an angle between the first wall 520 and the second wall 522 of the body 516 of the first disc replacement trial component 540 can be different than a second angle between the first wall 520 and the second wall 522 of the body 516 of the second disc replacement trial component 542. In other instances, the first and second angles can be the same. The width of the trials can be short enough that the surgeon can confirm safe depth of the graft.

According to one method of use, in surgery, a surgeon first removes the intervertebral disc from between a pair of adjacent vertebrae of a patient. Then, the surgeon uses the plurality of disc replacement trial components 512 of the kit 510 to determine the necessary size of a disc replacement body to be inserted into the intervertebral space by individually and consecutively placing the plurality of disc replacement trial components 512 between the pair of adjacent vertebrae, until one of the plurality of disc replacement trial components 512 is deemed the correct size.

Once a trial is deemed the correct size, the surgeon can then drill pilot holes into the pair of adjacent vertebrae using the first through fourth bone-screw drill guide holes 532, 534, 536, 538. These pilot holes can then be used for the insertion of bone screws, which can be used to lock a spinal fixation system in place between the pair of adjacent vertebrae, as described with respect to the other embodiments of the invention above.

Figure 16:
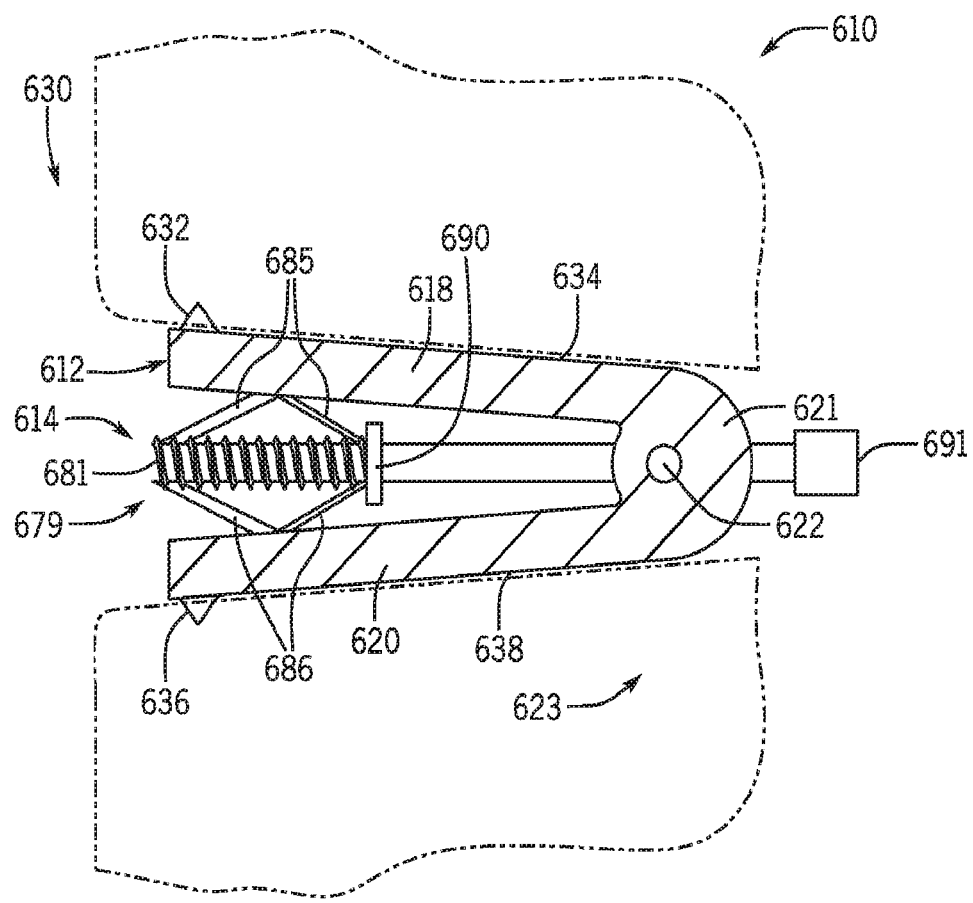
FIG. 16 is a side elevation view of a fourth embodiment of a spinal fixation system implanted on a spine.

Referring now to FIG. 16, there is shown a fourth embodiment of a spinal fixation system 610 according to the invention implanted on a spine. The spinal fixation system 610 includes an expandable disc replacement body 612, and an adjustment mechanism 614. The expandable disc replacement body 612 includes a first wall 618, a second wall 620, and a hinge 621 including a pin 622 attaching the first wall 618 and the second wall 620 at a posterior end 623 of the expandable disc replacement body 612.

The disc replacement body 612 may comprise a metallic material, such as titanium, cobalt chrome or stainless steel, or a polymeric material, such as polyetheretherketone.

The first wall 618 further includes a first bone anchor 632 on a superior surface 634 of the first wall 618. The first bone anchor 632 is configured to provide stabilization to the spinal fixation system 610 when the spinal fixation system 610 is implanted between two adjacent vertebrae, as also described below. Similarly, the second wall 620 further includes a second bone anchor 636 on an inferior surface 638 of the second wall 620. Again, the second bone anchor 636 is also configured to provide stabilization to the spinal fixation system 610 when the spinal fixation system 610 is implanted between two adjacent vertebrae, as also described below.

The adjustment mechanism 614 comprises a jack mechanism 679 including a leadscrew 681, two upper legs 685, and two lower legs 686. The leadscrew 681 further includes a head 690 on a posterior end of the leadscrew 681. The head 690 is configured to be posteriorly accessed and rotated by a screwdriver 691. The screwdriver 691 may be torque limited, to prevent excessive force that could fracture the adjacent vertebrae. Additionally, the two upper legs 685 are hingedly coupled to the first wall 618 at superior ends of the two upper legs 685 and are threadably coupled to the leadscrew 681 at inferior ends of the two upper legs 685. Similarly, the two lower legs 686 are hingedly coupled to the second wall 620 at inferior ends of the two lower legs 686 and are threadably coupled to the leadscrew 681 at superior ends of the two lower legs 686.

Now that the structure of the fourth embodiment of the spinal fixation system 610 has been described, the functionality of the spinal fixation system 610 will be described below.

According to one method of use, in surgery, a surgeon first removes an intervertebral disc from between two adjacent vertebrae of a patient. Then, the expandable disc replacement body 612 of the spinal fixation system 610 described above may be placed between the two adjacent vertebrae, such that the first wall 618 is adjacent the superior of the two vertebrae and the second wall 620 is adjacent the inferior of the two vertebrae. Then, once the expandable disc replacement body 612 is placed between the two adjacent vertebrae, the adjustment mechanism 614 can be used to achieve various angles between the first wall 618 and the second wall 620 of the expandable disc replacement body 612. The angles described herein are formed between the first wall 618 and the second wall 620, with the hinge 621 nominally forming the vertex of the angle.

As the leadscrew 681 is posteriorly rotated clockwise, the leadscrew 681 threadably engages the two upper legs 685, bringing the inferior ends of the two upper legs 685 towards each other. The leadscrew 681 similarly engages the two lower legs 686, bringing the superior ends of the two lower legs 686 towards each other. As the inferior ends of the two upper legs 685 and the superior ends of the two lower legs 686 are pulled towards each other by the leadscrew 681, the superior ends of the two upper legs 685 are forced away from the inferior ends of the two lower legs 686. This results in the first wall 618 being forced away from the second wall 620, thereby increasing an angle formed therebetween. When the expandable disc replacement body 612 is implanted between the two adjacent vertebrae, the angle between the first wall 618 and the second wall 620 is negative (i.e., the anterior ends of the first and second walls 618, 620 are closer than the posterior ends of the first and second walls 618, 620). As the leadscrew 681 is rotated, angle between the first wall 618 and the second wall 620 becomes less negative, and eventually, the first wall 618 becomes parallel with the second wall 620. When the first wall 618 is parallel with the second wall 620, the expandable disc replacement body 612 is considered to be in a neutral position. In some embodiments, as the leadscrew 681 is rotated, the spinal fixation system 610 can be configured to give a tactile feedback informing the surgeon when the expandable disc replacement body 612 has reached the neutral position. Further, as the first wall 618 and the second wall 620 are forced apart, the superior surface 634 of the first wall 618, and the inferior surface 638 of the second wall 620 contact the two adjacent vertebrae. As the superior surface 634 and inferior surface 638 come into contact with the two adjacent vertebrae, the first and second bone anchors 632, 636 slightly pierce the vertebrae, thereby providing stabilization to the spinal fixation system 610.

Additionally, when the leadscrew 681 is rotated, the rotation can correlate to a predetermined change in the angle between the first and second walls 618, 620. This capability to change the angle between the first and second walls 618, 620 allows for the expandable disc replacement body 612 to be used to counteract various degrees of lordosis of the spine. The leadscrew 681 can include markings on the head 690 wherein rotation of the head 690 from one marking to the adjacent marking correlates with a predetermined change in the angle between the first and second walls 618, 620.

In some embodiments, there may be a first jack mechanism and a second mechanism disposed on opposite lateral sides of the expandable disc replacement body 612. In these cases, the first and second jack mechanisms can be adjusted individually, thereby creating a first adjustment angle on a first lateral side that is different than a second adjustment angle on a second lateral side. The difference between the first and second adjustment angles may create a slight lateral angle between the first and second walls 618, 620, which may further be used to counteract scoliosis of the spine. In this case, the hinge 621 may alternatively be formed of a pliable material coupling the first and second walls 618, 620 to allow for biaxial rotation.

Figure 17:
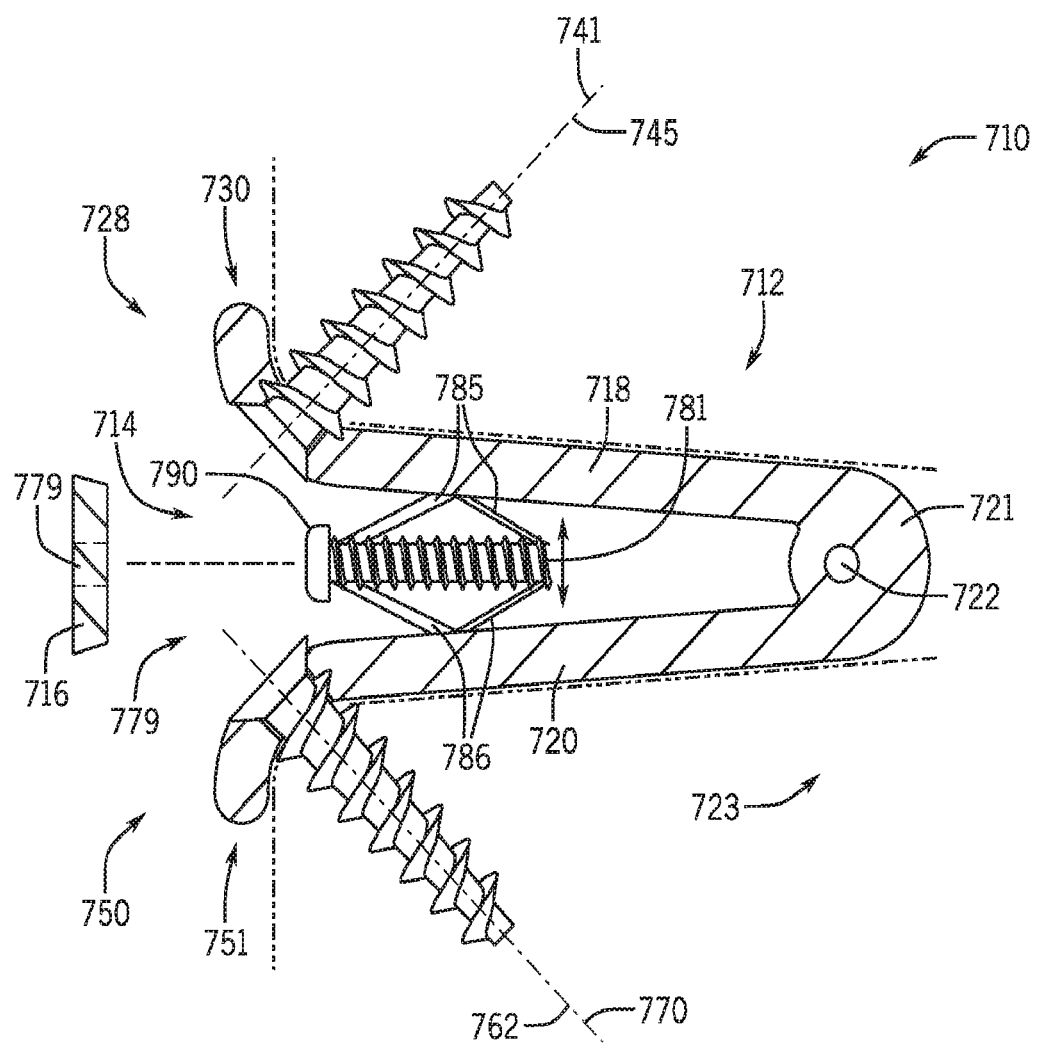
FIG. 17 is a side elevation view of a fifth embodiment of a spinal fixation system implanted on a spine.

Referring now to FIG. 17, there is shown a fifth embodiment of a spinal fixation system 710 according to the invention implanted on a spine. The spinal fixation system 710 is substantially similar to the spinal fixation system 10 described above, with like parts labeled with like numbers (e.g., first wall 18 and first wall 718, hinge 21 and hinge 721, etc.). The adjustment mechanism 714 of the spinal fixation system 710, however, comprises a jack mechanism 779. The jack mechanism 779 includes a leadscrew 781, two upper legs 785, and two lower legs 786. The leadscrew 781 further includes a head 790 on an anterior end of the leadscrew 781. The head 790 is configured to anteriorly accessed and rotated by a screwdriver (not shown). Additionally, the two upper legs 785 are hingedly coupled to the first wall 718 at superior ends of the two upper legs 785 and are threadably coupled to the leadscrew 781 at inferior ends of the two upper legs 785. Similarly, the two lower legs 786 are hingedly coupled to the second wall 720 at inferior ends of the two lower legs 786 and are threadably coupled to the leadscrew 781 at superior ends of the two lower legs 786.

Now that the structure of the fifth embodiment of the spinal fixation system 710 has been described, the functionality of the spinal fixation system 710 will be described below.

According to one method of use, in surgery, a surgeon first removes an intervertebral disc from between two adjacent vertebrae of a patient. Then, the expandable disc replacement body 712 of the spinal fixation system 710 described above may be placed between the two adjacent vertebrae, such that the first wall 718 is adjacent the superior of the two vertebrae and the second wall 720 is adjacent the inferior of the two vertebrae. Then, once the expandable disc replacement body 712 is placed between the two adjacent vertebrae, the adjustment mechanism 714 can be used to achieve various angles the first wall 718 and the second wall 720 of the expandable disc replacement body 712.

As the leadscrew 781 is anteriorly rotated clockwise, the leadscrew 781 threadably engages the two upper legs 785, bringing the inferior ends of the two upper legs 785 towards each other. The leadscrew 781 similarly engages the two lower legs 786, bringing the superior ends of the two lower legs 786 towards each other. As the inferior ends of the two upper legs 785 and the superior ends of the two lower legs 786 are pulled towards each other by the leadscrew 781, the superior ends of the two upper legs 785 are forced away from the inferior ends of the two lower legs 786. This results in the first wall 718 being forced away from the second wall 720, thereby increasing an angle formed therebetween. As such, when the leadscrew 781 is rotated, the rotation can correlate to a predetermined change in the angle between the first and second walls 718, 720. This capability to change the angle between the first and second walls 718, 720 allows for the expandable disc replacement body 712 to be used to counteract various degrees of lordosis of the spine. The leadscrew 781 can include markings on the head 790 wherein rotation of the head 790 from one marking to the adjacent marking correlates with a predetermined change in the angle between the first and second walls 718, 720.

In some embodiments, there may be a first jack mechanism and a second mechanism disposed on opposite lateral sides of the expandable disc replacement body 712. In these cases, the first and second jack mechanisms can be adjusted individually, thereby creating a first adjustment angle on a first lateral side that is different than a second adjustment angle on a second lateral side. The difference between the first and second adjustment angles may create a slight lateral angle between the first and second walls 718, 720, which may further be used to counteract scoliosis of the spine. In this case, the hinge 721 may alternatively be formed of a pliable material coupling the first and second walls 718, 720 to allow for biaxial rotation.

Figure 18:
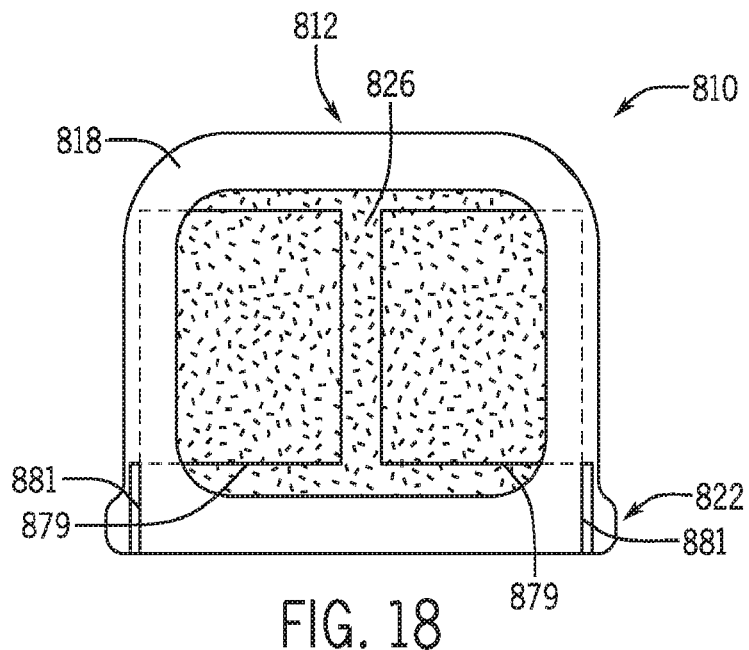
FIG. 18 is a top plan view of a sixth embodiment of a spinal fixation system implanted on a spine, shown with deployable wings in a retracted position.
Figure 19:
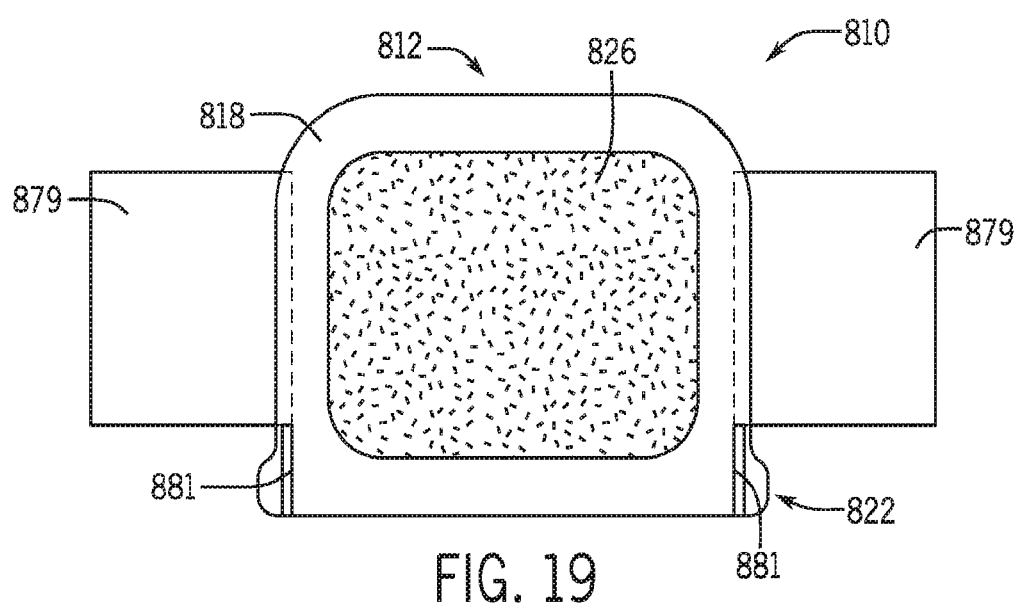
FIG. 19 is a top plan view of the spinal fixation system of FIG. 18, shown with the deployable wings in an extended position.

Turning now to FIGS. 18 and 19, there is shown a sixth embodiment of a spinal fixation system 810 according to the invention implanted on a spine. The spinal fixation system 810 includes a disc replacement body 812. The disc replacement body 812 includes a first wall 818 and a second wall (not shown) opposite the first wall 818. In some embodiments, the first wall 818 and the second wall can be substantially parallel. In some other embodiments, the first wall 818 and the second wall can be angled such that a first distance between the first wall 818 and the second wall at a proximal end 822 of the disc replacement body 812 is larger than a second distance between the first wall 818 and the second wall at a distal end 823 of the disc replacement body 812. The first wall 818 and the second wall further include a bone graft chamber 826 formed therebetween and capable of receiving bone graft.

The spinal fixation system 810 further includes a pair of wings 879 disposed on a superior surface of the spinal fixation system 810. The pair of wings 879 are deployable from a retracted position (as shown in FIG. 18) to an extended position (as shown in FIG. 19). The spinal fixation system 810 also includes a pair of locking pins 881 on the proximal end 822 of the disc replacement body 812 configured to engage the pair of wings 879, thereby locking them in place.

Having described the structure of the sixth embodiment of the spinal fixation system 810, the functionality of the spinal fixation system 810 will be described below.

According to one method of use, in surgery, a surgeon first removes an intervertebral disc from between two adjacent vertebrae of a patient, with the pair of wings 879 in the retracted position. Then, the disc replacement body portion 812 of the spinal fixation system 810 described above may be placed between the two adjacent vertebrae, such that the first wall 818 is adjacent a superior of the two vertebrae and the lower wall is adjacent an inferior of the two vertebrae.

Once the disc replacement body 812 is placed between the two adjacent vertebrae, the surgeon can deploy the pair of wings 879 from the retracted position to the extended position. With the pair of wings 879 in the extended position, the contact surface (i.e., the amount of surface area of the disc replacement body 812 making contact with the adjacent vertebrae) is greatly increased. This increase in contact surface can reduce the local stress (i.e., point pressure) experienced by the adjacent vertebrae, and thereby lower subsidence risk. The increase in contact surface can also increase friction between the disc replacement body 812 and the adjacent vertebrae, aiding in stabilizing the spinal fixation system 810 while the spinal fixation system 810 is implanted in the spine, aiding in the prevention of backout into the spinal canal and resultant neurological compression.

Once the pair of wings 879 are deployed, the locking pins 881 can be used to lock the pair of wings 879 in place, acting as rigidly fixed lateral extensions.

Figure 20:
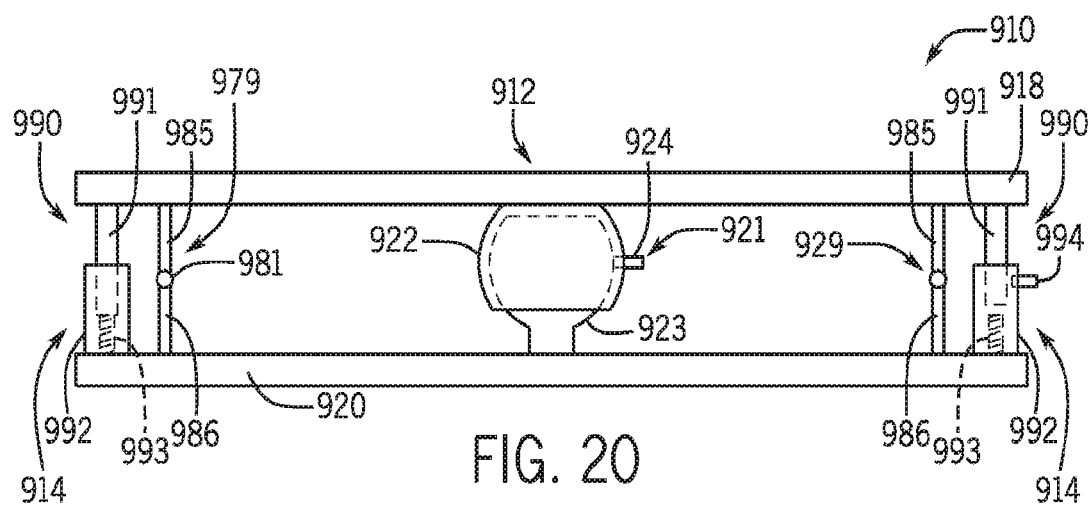
FIG. 20 is a front elevation view of a seventh embodiment of a spinal fixation system.
Figure 21:
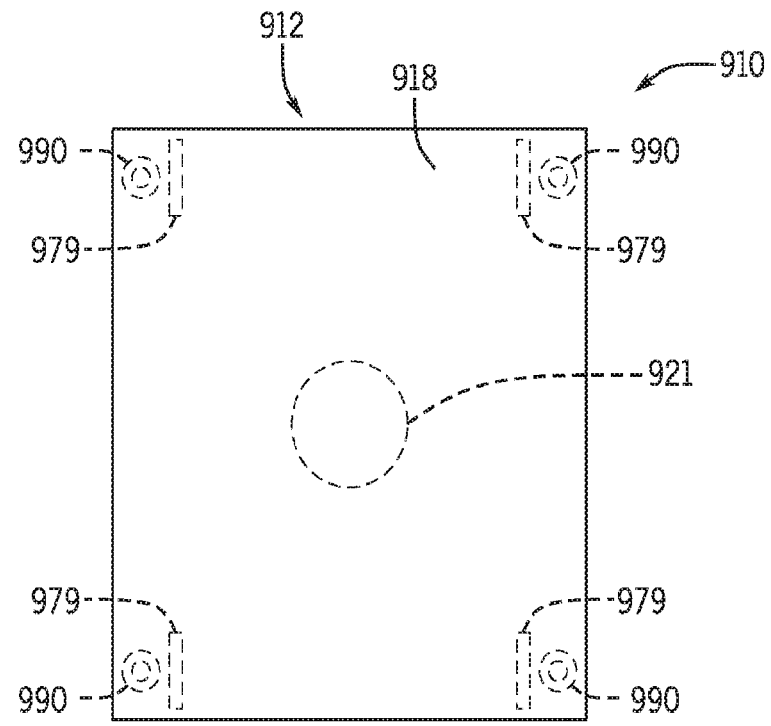
FIG. 21 is a top plan view of the spinal fixation system of FIG. 20.
Figure 22:
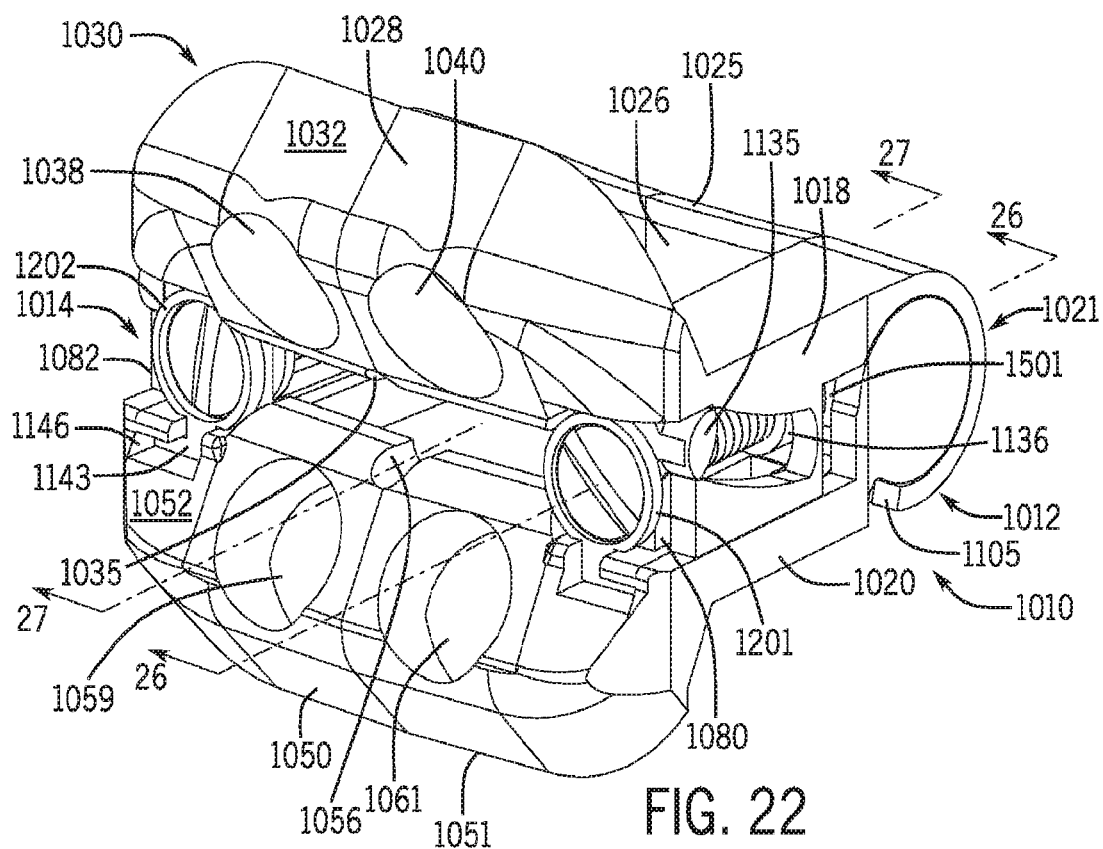
FIG. 22 is a front perspective view of an eighth embodiment of a spinal fixation system.
Figure 23:
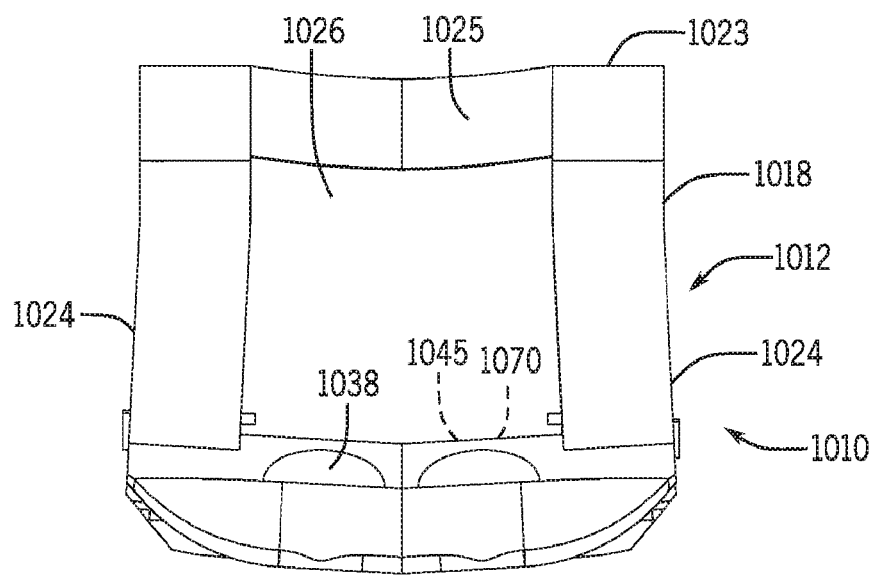
FIG. 23 is a top plan view of the spinal fixation system of FIG. 22.
Figure 24:
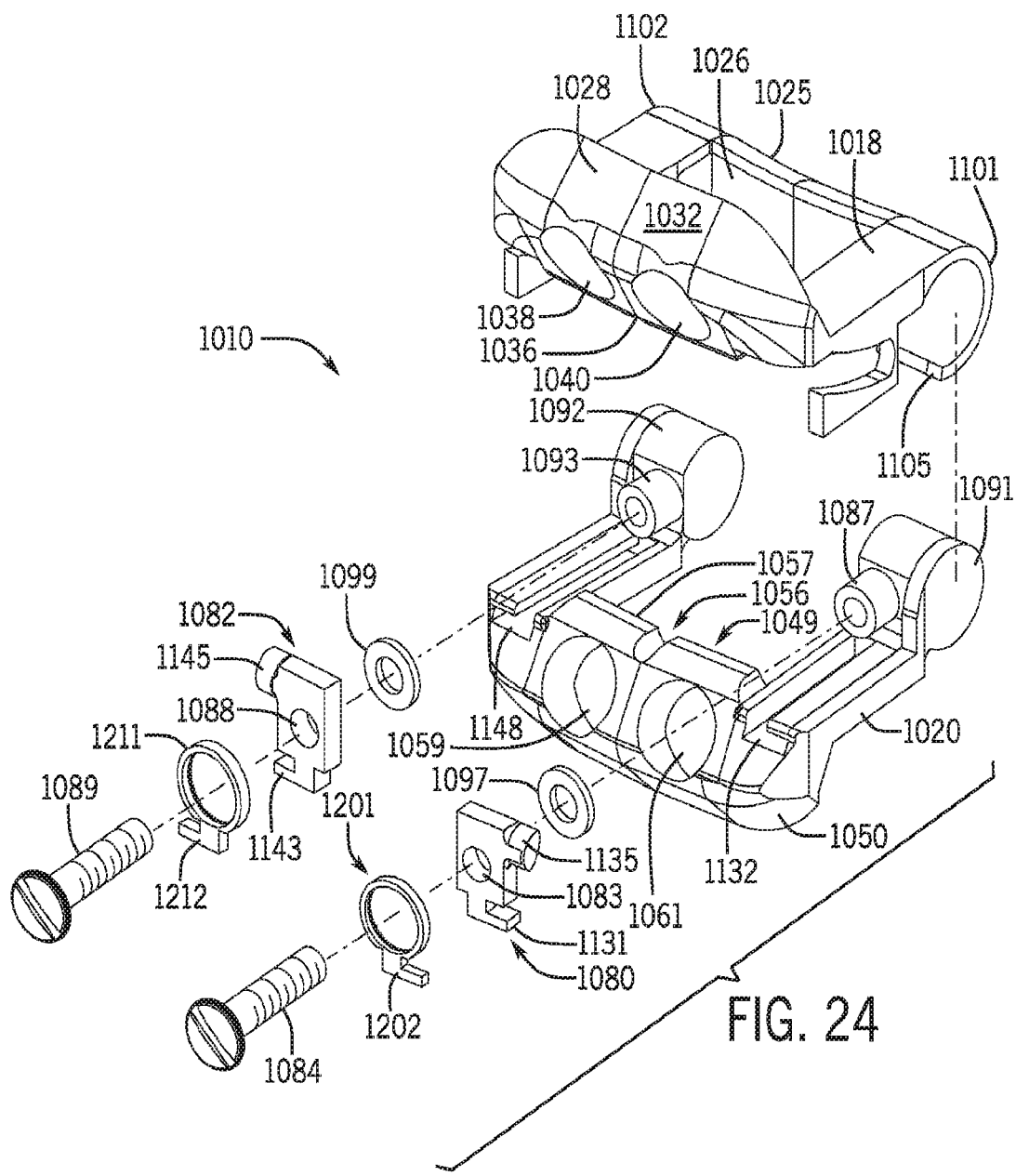
FIG. 24 is an exploded perspective view of the spinal fixation system of FIG. 22.
Figure 27:
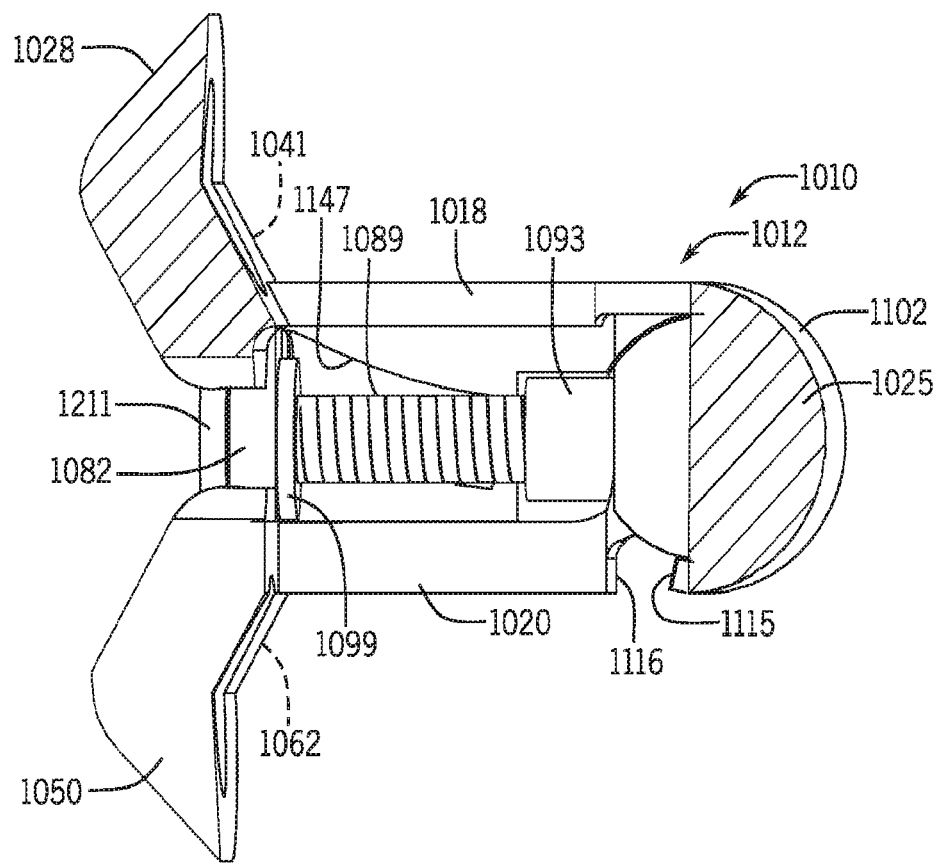
FIG. 27 is a cross-sectional view of the spinal fixation system of FIG. 22 taken along line 27-27 of FIG. 22.

Referring now to FIGS. 20 and 21, there is shown a seventh embodiment of a spinal fixation system 910 according to the invention implanted on a spine. The spinal fixation system 910 includes a disc replacement body 912 and a plurality of adjustment mechanisms 914. The disc replacement body 912 includes a first wall 918, a second wall 920, and a joint 921 connecting the first wall 918 and the second wall 920. The joint 921 further includes a socket portion 922, a ball portion 923 received in the socket portion 922, and a pin 924 configured to lock the joint 921, thereby preventing relative movement between the first wall 918 and the second wall 920. The disc replacement body 912 may comprise a metallic material, such as titanium, cobalt chrome, or stainless steel, or a polymeric material, such as polyetheretherketone. The first wall 918 and the second wall 920 may further be perforated. This perforation may provide channels for bone graft, such as allograft bone to grow through the first and second walls 918, 920. This bone-ingrowth allows for biological fixation of the spinal fixation system 910. Furthermore, the first wall 918 and the second wall 920 may have a slight concavity to better match the contours of the two adjacent vertebrae, thereby allowing for more symmetric pressure distribution.

The plurality of adjustment mechanisms 914 includes four jack mechanisms 979 similar to the jack mechanism 679. Each of the jack mechanisms 979 similarly include a leadscrew 981, two upper legs 985, and two lower legs 986. Each leadscrew 981 further includes a head (not shown) that is configured to be accessed and rotated by a screwdriver (not shown). Additionally, the two upper legs 985 are hingedly coupled to the first wall 918 at superior ends of the two upper legs 985. Similarly, the two lower legs 986 are hingedly coupled to the second wall 920 at inferior ends of the two lower legs 986 and are threadably coupled to the leadscrew 981 at superior ends of the two lower legs 986.

Each of the plurality of adjustment mechanisms 914 further include a locking mechanism 990 including a rod 991, a cylinder 992, a spring 993, and a locking pin 994. The rod 991 is rigidly fixed to the first wall 918 and is partially enveloped by the cylinder 992. The cylinder 992 is rigidly fixed to the second wall 920. The spring 993 is disposed within the cylinder 992 between the second wall 920 and the rod 991. The spring 993 biases the rod 991 away from the second wall 920. The plurality of adjustment mechanisms 914 are disposed at corners of the disc replacement body 912. As such, the springs 993 of each of the plurality of adjustment mechanisms 914 bias the first wall 918 and the second wall 920 into a generally parallel configuration. The locking pin 994 is configured to lock the rod 991 relative to the cylinder 992, thereby rigidly fixing the locking mechanism 990.

Now that the structure of the seventh embodiment of the spinal fixation system 910 has been described, the functionality of the spinal fixation system 910 will be described below.

According to one method of use, in surgery, a surgeon first removes an intervertebral disc from between two adjacent vertebrae of a patient. Then, the disc replacement body 912 of the spinal fixation system 910 described above may be placed between the two adjacent vertebrae, such that the first wall 918 is adjacent the superior of the two vertebrae, such that the first wall 918 is adjacent the superior of the two vertebrae and the second wall 920 is adjacent the inferior of the two vertebrae. Then, once the disc replacement body 912 is place between the two adjacent vertebrae, the plurality of adjustment mechanisms 914 can be used to achieve various angles between the first wall 918 and the second wall 920 of the disc replacement body 912. The plurality of adjustment mechanisms 914, disposed at the corners of the disc replacement body 912, may further provide multi-planar spinal correction.

An advantage of this embodiment, is that multi-planar correction through the disc space, which is the natural mobile separation between elements of the spinal column, eliminates or reduces the need for osteotomies which create false separations to allow for similar multi-planar corrections. A further advantage is that this technique allows for improved precision. Traditional osteotomies result in angular correction based on the angle and magnitude of osteotomy cuts. This is far less precise that the method taught here.

As the leadscrews 981 of each of the plurality of jack mechanisms 979 are rotated, the first wall 918 and the second wall 920 can be forced apart at a corresponding corner of the disc replacement body 912. As the first wall 918 and the second wall 920 at one corner are forced apart, the first wall 918 and the second wall 920 rotate about the joint 921, resulting in the first wall 918 and the second wall 920 being forced together at an opposing corner.

Once the surgeon adjusts the plurality of adjustment mechanism 914 to achieve a desired angle, the surgeon can use the pin 924 to lock the joint 921 and can further additionally or alternatively use the locking pins 994 rigidly fix the locking mechanisms 990, thereby locking the first wall 918 relative to the second wall 920.

Referring now to FIGS. 22 to 27, there is shown an eighth embodiment of a spinal fixation system 1010 according to the invention. The spinal fixation system 1010 includes an expandable disc replacement body 1012, and an adjustment mechanism 1014. The expandable disc replacement body 1012 includes a first wall 1018, a second wall 1020, a hinge 1021 attaching the first wall 1018 and the second wall 1020 at a distal end 1023 of the expandable disc replacement body 1012, and two lateral sides 1024. The disc replacement body 1012 may comprise a metallic material, such as titanium, cobalt chrome or stainless steel, a polymeric material, such as polyetheretherketone, or a ceramic material.

The first wall 1018 of the expandable disc replacement body 1012 includes a first space 1026 for receiving bone graft, such as allograft bone, and a first bone-screw receiving section 1028 located on a proximal end 1030 of the first wall 1018. The first bone-screw receiving section 1028 includes a first flange 1032, and a first grasping recess 1035 on an inferior edge 1036 of the first bone-screw receiving section 1028. The first bone-screw receiving section 1028 is angled back from vertical to decrease the profile. The first flange 1032 may terminate in an overhang to prevent bone graft from backing out of the first space 1026. The first flange 1032 includes a first opening 1038 and a second opening 1040. The first opening 1038 defines a first longitudinal axis 1041, and is configured to receive a first bone screw. The second opening 1040 similarly defines a second longitudinal axis 1045, and is configured to receive a second bone screw. The first longitudinal axis 1041 and the second longitudinal axis 1045 diverge in a direction toward the distal end 1023 of the expandable disc replacement body 1012. First and second snap rings and snap ring recesses, which are identical to snap ring 77 and snap ring recess 78 illustrated in FIGS. 5 and 6, can be used in the first opening 1038 and the second opening 1040 to effectively block the first and second bone screws from backing out. The first flange 1032 may include additional holes at medial and lateral end sections of the first flange 1032 so that sutures can be threaded through the holes and tied to hold the expandable disc replacement body 1012 in place.

The second wall 1020 of the expandable disc replacement body 1012 includes a second space 1049 for receiving bone graft, and a second bone-screw receiving section 1050 located on a proximal end 1051 of the second wall 1020. The second bone-screw receiving section 1050 may angled back from vertical to decrease the profile. The second bone-screw receiving section 1050 includes a second flange 1052, and a second grasping recess 1056 located on a superior edge 1057 of the second bone-screw receiving section 1050. The second flange 1052 may terminate in an overhang to prevent bone graft from backing out of the second space 1049. The second flange 1052 includes a third opening 1059 and a fourth opening 1061. The third opening 1059 defines a third longitudinal axis 1062, and is configured to receive a third bone screw. The fourth opening 1061 defines a fourth longitudinal axis 1070, and is configured to receive a fourth bone screw 72. The third longitudinal axis 1062 and the fourth longitudinal axis 1070 also diverge in a direction toward the distal end 1023 of the expandable disc replacement body 1012. Third and fourth snap rings and snap ring recesses, which are identical to snap ring 77 and snap ring recess 78 illustrated in FIGS. 5 and 6, can be used in the third opening 1059 and the fourth opening 1061 to effectively block the third and fourth bone screws from backing out. The second flange 1052 may include additional holes at medial and lateral end sections of the second flange 1052 so that sutures can be threaded through the holes and tied to hold the expandable disc replacement body 1012 in place.

The hinge 1021 of the expandable disc replacement body 1012 is formed using a first arcuate structure 1101 at the distal end of the first wall 1018, an opposed second arcuate structure 1102 at the distal end of the first wall 1018, a first cylindrical structure 1091 at the distal end of the second wall 1020, and a second cylindrical structure 1092 at the distal end of the second wall 1020. The first arcuate structure 1101 surrounds the first cylindrical structure 1091 for rotation of the first arcuate structure 1101 with respect to the first cylindrical structure 1091, and the second arcuate structure 1102 surrounds the second cylindrical structure 1092 for rotation of the second arcuate structure 1102 with respect to the second cylindrical structure 1092. The hinge 1021 comprises a bar 1025 connecting the first arcuate structure 1101 and the second arcuate structure 1102. The bar 1025 is convex on a side facing the first space 1026 of the first wall 1018.

A first arcuate length of the first arcuate structure 1101 is used to limit the angular rotation of the first arcuate structure 1101 about the first cylindrical structure 1091 in that a terminal end 1105 of the first arcuate structure 1101 contacts a stop wall 1106 that extends from the first cylindrical structure 1091. The angular location of the terminal end 1105 of the first arcuate structure 1101 is determined by varying the first arcuate length of the first arcuate structure 1101. Likewise, a second arcuate length of the second arcuate structure 1102 is used to limit the angular rotation of the second arcuate structure 1102 about the second cylindrical structure 1092 in that a terminal end 1115 of the second arcuate structure 1102 contacts a stop wall 1116 that extends from the second cylindrical structure 1092. The angular location of the terminal end 1115 of the second arcuate structure 1102 is determined by varying the second arcuate length of the second arcuate structure 1102. In one non-limiting embodiment, the angular rotation of the first arcuate structure 1101 about the first cylindrical structure 1091 and the angular rotation of the second arcuate structure 1102 about the second cylindrical structure 1092 can be varied between a lower value of the angle of 0° and an upper value of the angle of 12°.

In order to easily assemble the spinal fixation system 1010, slots 1501, 1502 can be arranged in the lateral sidewalls of the first flange 1032. The first flange 1032 can slide onto the second flange 1052.

The adjustment mechanism 1014 comprises a first wedge 1080. A lower tab 1131 of the first wedge 1080 slidably engages the second wall 1020 in a channel 1132 of the second wall 1020. The first wedge 1080 includes a first wedge screw aperture 1083 configured to receive a first wedge translating screw 1084. The first wedge translating screw 1084 threadably engages a first internally threaded cylinder 1087, which is a portion of the first cylindrical structure 1091. A washer 1097 is at the distal side of the first wedge 1080 to prevent the first wedge 1080 from sliding out of place by moving distally on the screw 1084. Optionally, a guide post can also be located in the channel 1132 for extending into a guide hole of the first wedge 1080. The first wedge 1080 includes a lateral protrusion 1135 that moves in a first guide channel 1136 of the first wall 1018, and engages an inner surface 1137 of the first guide channel 1136. Optionally, the first wedge 1080 may further include a lower lateral protrusion that moves in a guide channel of the second wall 1020 similar to guide channel 1136 of the first wall 1018. In another option, the guide post located in the channel 1132 could be threaded and used to guide a jam nut until it rests flush with the first wedge 1080. The jam nut could also screw into receiving threads in the first wedge 1080. This mechanism would prevent the first wedge translating screw 1084, used in the first wedge 1080, from backing out/further penetrating the expandable disc replacement body 1012 due to micro-motion and vibration. The jam nut would be threaded onto the post as a final step in the procedure, once the angle of the expandable disc replacement body 1012 has been set, the bone graft inserted, and the expandable disc replacement body 1012 has been compressed to help secure the graft.

In another option, the guide post could function differently as a tine (no threads), and be bent superiorly to block the first wedge translating screw 1084 from backing out. Once the final position of the expandable disc replacement body 1012 has been set, the tine could be bent upward, into the screw head's slot. The slot could be modified to include more than one final vertical position required to receive the tine. For example, an "X" shape pattern, or a "+" shape pattern, or a "*" shape pattern could be incorporated on the screw head, lending more final angle position options (rather than being confined to integer angle values at each full turn). Using this principle, if the tine is bent into the screw head's slot, the screw cannot turn, and therefore will not back-out/protrude after its final position is set.

The adjustment mechanism 1014 comprises a second wedge 1082. A lower tab 1143 of the second wedge 1082 slidably engages the second wall 1020 in a channel 1144 of the second wall 1020. The second wedge 1082 includes a second wedge screw aperture 1088 configured to receive a second wedge translating screw 1089, similar to the first wedge 1080. The second wedge translating screw 1089 threadably engages a second internally threaded cylinder 1093, which is a portion of the second cylindrical structure 1092. A washer 1099 is at the distal side of the second wedge 1082 to prevent the second wedge 1082 from sliding out of place by moving distally on the screw 1089. Optionally, a guide post can also be located in the channel 1144 for extending into a guide hole of the second wedge 1082. The second wedge 1082 includes a lateral protrusion 1145 that moves in a second guide channel 1146 of the first wall 1018, and engages an inner surface 1147 of the second guide channel 1146. Optionally, the second wedge 1082 may further include a lower lateral protrusion that moves in a guide channel of the second wall 1020 similar to guide channel 1146 of the first wall 1018. In another option, the guide post could be threaded and used to guide a jam nut until it rests flush with the second wedge 1082 as described above with reference to the first wedge 1080.

In another option, the guide post could function differently as a tine (no threads), and be bent superiorly to block the second wedge translating screw 1089 from backing out. Once the final position of the expandable disc replacement body 1012 has been set, the tine could be bent upward, into the screw head's slot. The slot could be modified to include more than one final vertical position required to receive the tine. For example, an "X" shape pattern, or a "+" shape pattern, or a "*" shape pattern could be incorporated on the screw head, lending more final angle position options (rather than being confined to integer angle values at each full turn). Using this principle, if the tine is bent into the screw head's slot, the screw cannot turn, and therefore will not back-out/protrude after its final position is set.

Now that the structure of the eighth embodiment of the spinal fixation system 1010 has been described, the functionality of the spinal fixation system 1010 will be described below. According to one method of use, in surgery, a surgeon first removes an intervertebral disc from between two adjacent vertebrae of a patient. Then, the expandable disc replacement body 1012 of the spinal fixation system 1010 described above may be placed between the two adjacent vertebrae, such that the first bone-screw receiving section 1028 is adjacent the superior of the two vertebrae and the second bone-screw receiving section 1050 is adjacent the inferior of the two vertebrae, which may be done using the disc replacement holder 93. Then, using the four angled drill guide holes 99 on the interface block 96 of the disc replacement holder 93, pilot holes may be drilled into the superior and inferior vertebrae to aid in the insertion of the first through fourth bone screws into the vertebrae. A sounding rod may be inserted through the drill guide holes 99 into the pilot holes.

Once the expandable disc replacement body 1012 is placed between the two adjacent vertebrae, the first and second bone screws may be screwed into the superior vertebra through the first and second openings 1038, 1040, respectively, and the third and fourth bone screws may be screwed into the inferior vertebra through the third and fourth openings 1059, 1061, respectively.

After the first through fourth bone screws are in place, the expandable disc replacement body 1012 is effectively locked between the two adjacent vertebrae. At this point, the adjustment mechanism 1014 can be used to achieve various angles between the first wall 1018 and the second wall 1020 of the expandable disc replacement body 1012.

As first and second wedge translating screws 1084, 1089 are rotated clockwise, they force the first and second wedges 1080, 1082 towards the distal end 1023 of the expandable disc replacement body 1012. Due to the distally directed movement of the lateral protrusion 1135 of the first wedge 1080 in the first guide channel 1136 of the first wall 1018, the first wedge 1080 forces the first and second walls 1018, 1020 to separate. Likewise, due to the distally directed movement of the lateral protrusion 1145 of the second wedge 1082 in the second guide channel 1146 of the first wall 1018, the second wedge 1082 also forces the first and second walls 1018, 1020 to separate. Because the first and second walls 1018, 1020 are coupled at the hinge 1021, this separation increases an angle formed therebetween. As such, when the first and second wedge translating screws 1084, 1089 are rotated, the rotation can correlate to a predetermined change in the angle between the first and second walls 1018, 1020. This capability to change the angle between the first and second walls 1018, 1020 allows for the expandable disc replacement body 1012 to be used to counteract various degrees of lordosis of the spine. The first and second wedge translating screws 1084, 1089 can include markings on the screw head wherein rotation of the screw head from one marking to the adjacent marking correlates with a predetermined change in the angle between the first and second walls 1018, 1020. The first wedge 1080 and the second wedge 1082 can also be inserted unequal amounts to create a first adjustment angle between the first and second walls 1018, 1020 on one lateral side 1024 of the expandable disc replacement body 1012, and a different second adjustment angle between the first and second walls 1018, 1020 on the other lateral side 1024 of the expandable disc replacement body 1012. The difference between the first and second adjustment angles may create a slight lateral angle between the first and second walls 1018, 1020, which may further be used to counteract scoliosis of the spine. In this case, the hinge 1021 may alternatively be formed of a pliable material coupling the first and second walls 1018, 1020 to allow for biaxial rotation.

When the first and second wedge translating screws 1084, 1089 are rotated to their positions that correlate to a predetermined angle between the first and second walls 1018, 1020, locking rings 1201, 1211 can effectively block the first and second wedge translating screws 1084, 1089 from backing out. The locking ring 1201 includes a lower tab 1202 that slidably engages the second wall 1020 in the channel 1132 of the second wall 1020. Thus, the locking ring 1201 can be held in a locking position in contact with the first wedge translating screw 1084 blocking the first wedge translating screw 1084 from backing out. The locking ring 1201 can be moved into contact with the head of the first wedge translating screw 1084 by pressing the locking ring 1201 toward the first wedge translating screw 1084.

Likewise, locking ring 1211 includes a lower tab 1212 that slidably engages the second wall 1020 in the channel 1146 of the second wall 1020. When the second wedge translating screw 1089 is rotated to its position that correlates to a predetermined angle between the first and second walls 1018, 1020, the locking ring 1211 can be moved into contact with the head of the second wedge translating screw 1089 by pressing the locking ring 1211 toward the second wedge translating screw 1089.

Thus, the locking rings 1201, 1211 ride in front of the screw head as the screw is moved freely until the final position of the expandable disc replacement body 1012 is achieved. Once the final position is achieved, the locking rings 1201, 1211 can be pushed into place by tapping/hitting the locking rings 1201, 1211 with force. The locking rings 1201, 1211 can include teeth. A design featuring numerous teeth provides the greatest freedom. The surgeon is not confined to locking the expandable disc replacement body 1012 at angles of integer value, nor is the surgeon confined to locking the expandable disc replacement body 1012 at largely spaced intervals (i.e., 3.2, 3.4, 3.6, 3.8 degrees), as a square or hex shaped head would imply. Alternatively, the screw head could be modified to be a square, hex, or Torx (star) shape. The locking rings 1201, 1211 can be modified to match the shape of the screw head, depending on the shape chosen.

Figure 28A:
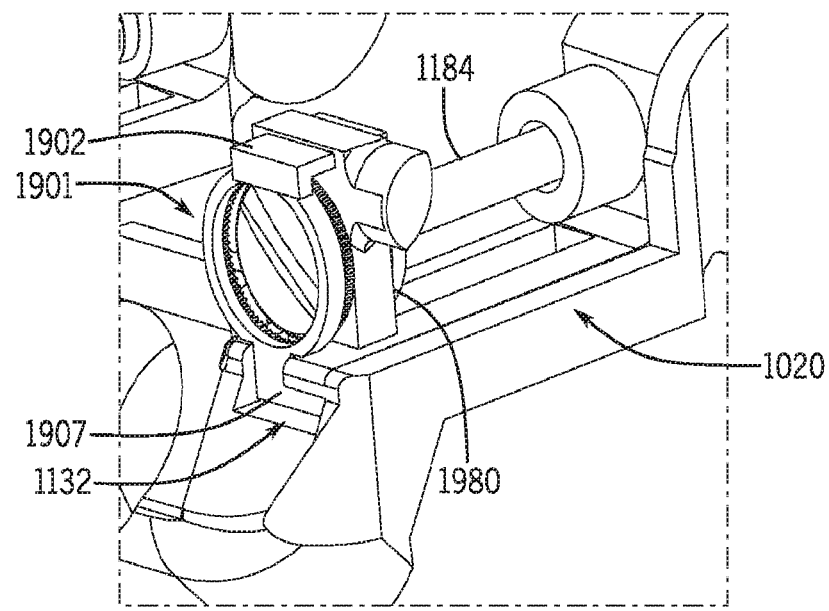
FIG. 28A is a front partial perspective view of a screw locking mechanism of a ninth embodiment of a spinal fixation system.
Figure 28B:
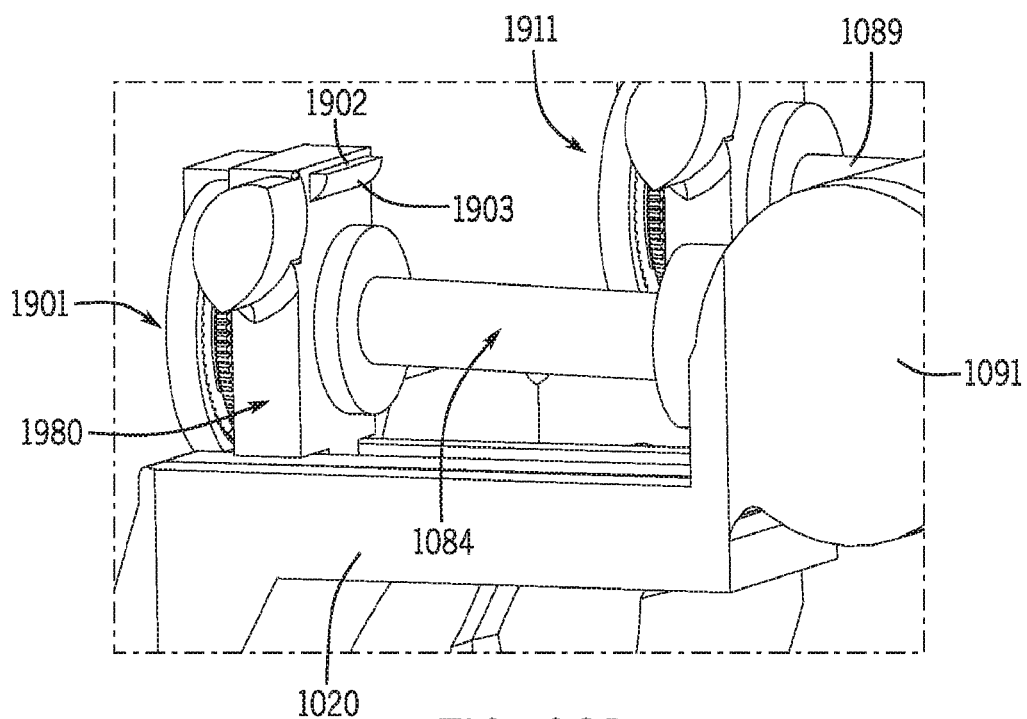
FIG. 28B is a rear partial perspective view of the screw locking mechanism of FIG. 28A.

Alternatively, as shown in FIGS. 28A-28B, an alternative locking ring 1901 can effectively block the first wedge translating screw 1084 from backing out. The locking ring 1901 includes a superior projection 1902 that is inserted through a slot 1903 in a first wedge 1980. The projection 1902 can be bent upward where the projection 1902 extends beyond a distal end of the slot 1903 preventing the locking ring 1901 from moving out of its intended position. The locking ring 1901 also includes a lower tab 1907 that slidably engages the second wall 1020 in the channel 1132 of the second wall 1020. Thus, the locking ring 1901 can be held in a locking position in contact with the first wedge translating screw 1084 blocking the first wedge translating screw 1084 from backing out. The locking ring 1901 would be positioned with the locking ring 1901 spaced from the first wedge translating screw 1084 and the projection 1901 bent upward as part of the manufacturing/assembly process. The surgeon would receive the part as one assembly attached to the first wedge 1080, eliminating the need for a free floating, additional piece. When the first wedge translating screw 1084 is rotated to its position that correlates to a predetermined angle between the first and second walls 1018, 1020, the locking ring 1901 can be moved into contact with the head of the first wedge translating screw 1084 by pressing the locking ring 1901 toward the first wedge translating screw 1084. The projection 1902 can be bent further upward to lock the locking ring 1901 against the first wedge translating screw 1084 thereby blocking the first wedge translating screw 1084 from backing out. Likewise, a locking ring 1911, similar to locking ring 1901, can be used in the same manner to blocking a second wedge translating screw 1089 from backing out.

Thus, the locking rings 1901, 1911 ride in front of the screw head as the screw is moved freely until the final position of the expandable disc replacement body 1012 is achieved. Once the final position is achieved, the locking rings 1901, 1911 will be pushed into place by tapping/hitting the locking rings 1901, 1911 with force. The locking rings 1901, 1911 can include teeth. A design featuring numerous teeth provides the greatest freedom. The surgeon is not confined to locking the expandable disc replacement body 1012 at angles of integer value, nor is the surgeon confined to locking the expandable disc replacement body 1012 at largely spaced intervals (i.e., 3.2, 3.4, 3.6, 3.8 degrees), as a square or hex shaped head would imply. Alternatively, the screw head could be modified to be a square, hex, or Torx (star) shape. The locking rings 1901, 1911 can be modified to match the shape of the screw head, depending on the shape chosen.

Alternatively, when the first and second wedge translating screws are rotated to their positions that correlate to a predetermined angle between the first and second walls 1018, 1020, locking plates can effectively block the first and second wedge translating screws from backing out. In the spinal fixation system 1810 of FIG. 29, a locking plate 1301 is shown. The locking plate 1301 includes posts 1303a, 1303b, 1303c that are inserted through slots 1203 in a first wedge 1080a. A fourth post is not shown in FIG. 29. The locking plate 1301 can be held in a locking position in contact with the first wedge translating screw 1084 blocking the first wedge translating screw 1084 from backing out. The locking plate 1301 would be positioned with the locking plate 1301 spaced from the first wedge translating screw 1084 (as shown in FIG. 29) as part of the manufacturing/assembly process. The surgeon would receive the part as one assembly attached to the first wedge 1080a, eliminating the need for a free floating, additional piece. When the first wedge translating screw 1084 is rotated to its position that correlates to a predetermined angle between the first and second walls 1018, 1020, the locking plate 1301 can be moved into contact with the head of the first wedge translating screw 1084 by pressing the locking plate 1301 toward the first wedge translating screw 1084. The locking plate 1301 is placed in contact with a screw head surface 1378 of the first wedge translating screw 1084 in a tight interference fit thereby blocking the first wedge translating screw 1084 from backing out. The shape of the locking interference fit could feature teeth 1376, in addition to a square, hex or Torx shaped head. A locking plate for the second wedge translating screw operates in the same manner as locking plate 1301.

Thus, the invention provides spinal fixation systems, multi-level spinal fixation systems, and kits for spinal surgery. Furthermore, it will be appreciated by those skilled in the art that elements of the various embodiments described herein can be used in conjunction to achieve desired results. The specific embodiments illustrated are exemplary and are not meant to be limiting. In this regard, the embodiments illustrated herein may refer to use for anterior cervical spine surgery. However, the spinal fixation systems and methods of the present disclosure are useful over the entire spine. For example, the spinal fixation systems and methods of the present disclosure can be used at the thoracic or lumbar spine. Furthermore, embodiments of this invention can be inserted via lateral entry as opposed to the anterior entry embodiments depicted in the figures. While the non-limiting embodiments of the present disclosure show an anterior cervical device that is applicable for all direct anterior use from C2 to S1 vertebrae, in the thoracic spine and lumbar spine, the spinal fixation systems of the present disclosure can be used as a lateral cage, that enters from the side and has the adjustment mechanism that can increase lordosis and/or correct coronal angulation (i.e., in scoliosis). Thus, the spinal fixation systems and methods of the present disclosure work beneficially from C2 to S1 vertebrae, with one difference being the scale of the expandable disc replacement body of the spinal fixation system.

Additionally, prior to the insertion of any of the described spinal fixation systems, a computer templating system can take specific measurements from preoperative imaging to define the native dimensions of the disc space (i.e., height, width, depth, and angulation between adjacent vertebrae) as well as global dimensions (i.e., height, depth, and angulation of a general spinal region). These dimensions can then be used to calculate a prescribed amount of correction (i.e., height and/or angulation degree) of each individual spinal fixation system, between multiple pairs of adjacent vertebrae, to achieve a desired global deformity correction. This prescribed correction can be multi-planar for both sagittal and coronal plane correction.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A spinal fixation system comprising:
an expandable disc replacement body including a first wall, a second wall, a hinge at a posterior position of the expandable disc replacement body hingedly coupling the first wall to the second wall, and a first bone-screw receiving section at an anterior position of the expandable disc replacement body and at a proximal end of the first wall, the first wall including a first bone contacting surface for engaging a superior vertebra of a spine, the second wall including a second bone contacting surface for engaging an inferior vertebra of the spine; and
an adjustment mechanism positioned between the first wall and the second wall, the adjustment mechanism includes a first wedge, a second wedge, a first wedge translating screw, a second wedge translating screw, a first internally threaded cylinder and a second internally threaded cylinder, wherein the first wedge and the second wedge are independent from each other and slidably engage the first and second walls,
wherein the first wedge includes a first wedge screw aperture for receiving the first wedge translating screw which is threadably connected to the first internally threaded cylinder that is directly coupled to a first lateral side of the hinge of the expandable disc replacement body at the posterior position,
wherein the second wedge includes a second wedge screw aperture for receiving the second wedge translating screw which is threadably connected to the second internally threaded cylinder that is directly coupled to a second lateral side of the hinge of the expandable disc replacement body at the posterior position, wherein the second lateral side is opposite to the first lateral side,
wherein an angle between the first wall and the second wall is configured to be continuously varied between a lower value of the angle and an upper value of the angle by rotating either of the first wedge translating screw and the second wedge translating screw to slide the corresponding one of the first wedge and second wedge from the anterior position towards the posterior position along the first and second walls to pivot the first wall relative to the second wall about the hinge at the posterior position.

2. The system of claim 1 wherein:
the expandable disc replacement body includes a second bone-screw receiving section at a proximal end of the second wall.

3. The system of claim 2 wherein:
the second bone-screw receiving section has a third opening for receiving a third bone screw, the third opening having a third longitudinal axis and
the second bone-screw receiving section has a fourth opening for receiving a fourth bone screw, the fourth opening having a fourth longitudinal axis and
the third longitudinal axis and the fourth longitudinal axis diverge in a direction toward a distal end of the expandable disc replacement body.

4. The system of claim 3 wherein:
the third opening includes a third snap ring recess containing a third snap ring, and
the fourth opening includes a fourth snap ring recess containing a fourth snap ring.

5. The system of claim 4 wherein:
when the third bone screw is received within the third opening, the third snap ring expands into the third snap ring recess to allow entry of the third bone screw and once the third bone screw passes the third snap ring, the third snap ring contracts, effectively blocking the third bone screw from backing out, and
when the fourth bone screw is received within the fourth opening, the fourth snap ring expands into the fourth snap ring recess to allow entry of the fourth bone screw and once the fourth bone screw passes the fourth snap ring, the fourth snap ring contracts, effectively blocking the fourth bone screw from backing out.

6. The system of claim 1 wherein:
the first bone-screw receiving section has a first opening for receiving a first bone screw, the first opening having a first longitudinal axis, and
the first bone-screw receiving section has a second opening for receiving a second bone screw, the second opening having a second longitudinal axis and
the first longitudinal axis and the second longitudinal axis diverge in a direction toward a distal end of the expandable disc replacement body.

7. The system of claim 6 wherein:
the first bone-screw receiving section has a first recessed edge between the first opening and the second opening.

8. The system of claim 6 wherein:
the first bone-screw receiving section has a first grasping recess between the first opening and the second opening.

9. The system of claim 8 further comprising:
a disc replacement holder including four angled drill guide holes and a grasping mechanism which detachably couples to the grasping recess of the first wall.

10. The system of claim 6 wherein:
the first opening includes a first snap ring recess containing a first snap ring, and
the second opening includes a second snap ring recess containing a second snap ring.

11. The system of claim 10 wherein:
when the first bone screw is received within the first opening, the first snap ring expands into the first snap ring recess to allow entry of the first bone screw and once the first bone screw passes the first snap ring, the first snap ring contracts, effectively blocking the first bone screw from backing out, and
when the second bone screw is received within the second opening, the second snap ring expands into the second snap ring recess to allow entry of the second bone screw and once the second bone screw passes the second snap ring, the second snap ring contracts, effectively blocking the second bone screw from backing out.

12. The system of claim 1 wherein,
the first wedge screw aperture includes a first wedge snap ring recess containing a first wedge snap ring.

13. The system of claim 12 wherein,
when the first wedge translating screw is received within the first wedge screw aperture, the first wedge snap ring expands into the first wedge snap ring recess to allow entry of the first wedge translating screw and once the first wedge translating screw passes the first wedge snap ring, the first wedge snap ring contracts, effectively blocking the first wedge translating screw from backing out.

14. The system of claim 1 wherein:
the rotation of either of the first wedge translating screw and the second wedge translating screw correlates to a predetermined change in the angle between the first and second walls.

15. The system of claim 1 wherein:
the first wedge and the second wedge are configured for sliding along the first and second wall in at least one of equal and unequal amount to make a first adjustment angle between the first wall and the second wall on one of the first and second lateral sides of the expandable disc replacement body same as or different than a second adjustment angle between the first wall and the second wall on another of the first and second lateral sides of the expandable disc replacement body.

16. The system of claim 1 wherein:
the first wall has a first space to allow for insertion of bone graft, and
the second wall has a second space to allow for insertion of bone graft.

17. The system of claim 1 wherein:
the hinge is formed by a pliable material.

18. The system of claim 1 wherein:
either of the first and second wedge translating screws is configured to provide a feedback indicating an increment of sliding of the corresponding first and second wedges relative to the first wall and the second wall.

19. The system of claim 18 wherein:
a head of either the first and second wedge translating screws includes markings which provides the feedback.

20. The system of claim 1 wherein:
at least one of the first bone contacting surface and the second bone contacting surface is a contoured bone engaging surface.

21. The system of claim 1 wherein:
the hinge comprises a pair of arcuate structures, a pair of cylindrical structures, one of the pair of arcuate structures surrounding one of the pair of cylindrical structures, the other of pair of arcuate structures surrounding the other of the pair of cylindrical structures,
the pair of arcuate structures is connected to at least one of the first wall and the second wall, and
the pair of cylindrical structures is connected to the other of the first wall and the second wall.

22. The system of claim 21 wherein:
an arcuate length of at least one of the pair of arcuate structures is used to limit the upper value of the angle by contacting one of the first wall and the second wall.

23. The system of claim 21 wherein:
the first wall has a first space to allow for insertion of bone graft, and
the hinge comprises a bar connecting the pair of arcuate structures or the pair of cylindrical structures.

24. The system of claim 23 wherein:
the bar is convex on a side facing the first space.

25. The system of claim 21 wherein:
one of the first wall and the second wall includes a pair of channels,
the first wedge includes a protrusion which extends into and is slidable in one of the pair of channels, and
the second wedge includes a protrusion which extends into and is slidable in the other of the pair of channels.

26. The system of claim 25 wherein:
the first wedge and the second wedge are located at the opposite first and second lateral sides of the first and second walls.

27. The system of claim 21 wherein:
the first wedge translating screw and the second wedge translating screw are configured to be inserted in unequal amounts to make a first adjustment angle between the first wall and the second wall on the first lateral side of the expandable disc replacement body different than a second adjustment angle between the first wall and the second wall on the second lateral side of the expandable disc replacement body.

28. The system of claim 1 wherein:
at least one of the first wall and the second wall includes a channel, and
the first wedge includes a protrusion which extends into and is slidable in the channel.

29. The system of claim 28 wherein:
the sliding of the first wedge is along an axis parallel to the second wall.

30. The system of claim 1 wherein:
the adjustment mechanism includes a locking component which prevents the adjustment mechanism from changing the angle between the first wall and the second wall when engaged with either of the first wedge translating screw and the second wedge translating screw, and at least one of the first wall and the second wall.

31. The system of claim 30 wherein:
the locking component comprises a locking tine if contacting the expandable disc replacement body configured to be inserted into a head of either of the first wedge translating screw and the second wedge translating screw in order to prevent further rotational motion.

32. The system of claim 30 wherein:

the locking component comprises a locking ring contacting the expandable disc replacement body configured to surround a head of either of the first wedge translating screw and the second wedge translating screw in order to prevent further rotational motion.

33. The system of claim 32 wherein:

the locking ring comprises at least one of teeth, one or more insertable posts, one or more insertable spades, a square cover, a hex cover, or a torx cover for contacting the head of either of the first wedge translating screw and the second wedge translating screw.

34. A multi-level spinal fixation system comprising:

a first spinal fixation system according to claim 1;

a second spinal fixation system according to claim 1; and a clamp dimensioned to couple together the first spinal fixation system according to claim 1 and the second spinal fixation system according to claim 1 when the first spinal fixation system according to claim 1 and the second spinal fixation system according to claim 1 are implanted in different intervertebral disc spaces.

\* \* \* \* \*

UNITED STATES PATENT AND TRADEMARK OFFICE
CERTIFICATE OF CORRECTION

PATENT NO. : 11,154,404 B2  
APPLICATION NO. : 16/331706  
DATED : October 26, 2021  
INVENTOR(S) : Brett Freedman et al.

It is certified that error appears in the above-identified patent and that said Letters Patent is hereby corrected as shown below:

In the Claims

Column 34, Claim 31, Lines 65-66, "tine if contacting" should be --tine contacting--.

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*